US010738304B2

(12) United States Patent
Kubo et al.

(10) Patent No.: US 10,738,304 B2
(45) Date of Patent: Aug. 11, 2020

(54) COMPLEX OF POLYSACCHARIDE AND DOUBLE-STRANDED RNA

(75) Inventors: Takanori Kubo, Hiroshima (JP); Hideki Ohba, Tosu (JP); Kazuo Sakurai, Kitakyushu (JP); Jusaku Minari, Kitakyushu (JP); Atsushi Uno, Koganei (JP)

(73) Assignee: NAPA JENOMICS CO., LTD., Koganei-Shi, Tokyo (JP)

( * ) Notice: Subject to any disclaimer, the term of this patent is extended or adjusted under 35 U.S.C. 154(b) by 0 days.

(21) Appl. No.: 12/808,504

(22) PCT Filed: Dec. 18, 2008

(86) PCT No.: PCT/JP2008/073125
§ 371 (c)(1),
(2), (4) Date: Aug. 27, 2010

(87) PCT Pub. No.: WO2009/078470
PCT Pub. Date: Jun. 25, 2009

(65) Prior Publication Data
US 2011/0111501 A1    May 12, 2011

(30) Foreign Application Priority Data
Dec. 18, 2007  (JP) ................................ 2007-326510

(51) Int. Cl.
*C12N 5/00*  (2006.01)
*C12N 15/11*  (2006.01)
*C07H 21/02*  (2006.01)

(52) U.S. Cl.
CPC ........ *C12N 15/111* (2013.01); *C12N 2310/14* (2013.01); *C12N 2310/3519* (2013.01); *C12N 2320/32* (2013.01); *C12N 2320/51* (2013.01)

(58) Field of Classification Search
CPC .................................................. C12N 15/111
USPC ....................................... 514/44 A; 536/24.5
See application file for complete search history.

(56) References Cited

FOREIGN PATENT DOCUMENTS

| EP | 1142591 B1 | 4/2008 |
|---|---|---|
| JP | 2004-261024 A | 9/2004 |
| JP | 2004261024 A | 9/2004 |
| JP | 2005-204612 A | 8/2005 |
| JP | 2005204612 A | 8/2005 |
| JP | 2005-255750 A | 9/2005 |
| JP | 2005255750 A | 9/2005 |
| JP | 2006-069913 A | 3/2006 |
| JP | 2006069913 A | 3/2006 |
| WO | 96/14873 A2 | 5/1996 |
| WO | 01/34207 A1 | 5/2001 |
| WO | WO2001034207 A1 | 5/2001 |
| WO | 2007/056153 A2 | 5/2007 |
| WO | 2007/069068 A2 | 6/2007 |

OTHER PUBLICATIONS

Translation of document JP 2005204612 A; published Aug. 4, 2005.*
Translation of document JP 2006069913 A; published Mar. 16, 2006.*
Caplen et al.; Specific inhibition of gene expression by small double-stranded RNAs in invertebrate and vertebrate systems; PNAS; vol. 98, No. 17; pp. 9742-9747; published Aug. 14, 2001.*
Han et al.; beta-1,3-Glucan-Induced Host Phospholipase D Activation Is Involved in Aspergillus fumigatus Internalization into Type II Human Pneumocyte A549 Cells; PLoS One; vol. 6, Issue 7: e21468; pp. 1-12; Jul. 8, 2011.*
European Search Report dated Feb. 2, 2011, corresponding with European Application No. 08862702.1, (6) pages.
Ryouji Karinaga et al., "Galactose-PEG dual conjugation of B-(1-3)-d-glucan schizophyllan for antisense oligonucleotides delivery to enhance the cellular uptake", Biomaterials, Elsevier Science Publishers BV., vol. 27, No. 8, pp. 1626-1635, Mar. 1, 2006.
Takahiro Matsumoto et al., "Chemically modified polysaccharide schizophyllan for antisense oligonucleotides delivery to enhance the cellular uptake efficiency", Biochimica et Biophysica Acta, Elsevier Science Publishers, vol. 1670, No. 2, pp. 91-104, Jan. 22, 2004.
Ryouji Karinaga et al., "PEG-appended beta-(1-3)-d-glucan schizophyllan to deliver antisense-oligonucleotides with avoiding lysosomal degradation", Biomaterials, Elsevier Science Publishers BV., vol. 26, No. 23, pp. 4866-4873, Aug. 1, 2005.
Masami Mizu et al., "Antisense oligonucleotides bound in the polysaccharide complex and the enhanced antisense effect due to the low hydrolysis", Biomaterials, Elsevier Science Publishers BV., vol. 25, No. 15, pp. 3117-3123, Jul. 1, 2004.
Takahise Anada et al., "Linear double-stranded DNA that mimics an infective tail of virus genome to enhance transfection", Journal of Controlled Release, Elsevier, vol. 108, No. 2-3, pp. 529-539, Nov. 28, 2005.
Theresa M. McIntire et al., "Observations of the (1-3)-β-D-Glucan Linear Triple Helix to Macrocycle Interconversion Using Noncontact Atomic Force Microscopy", J. Am. Chem. Society, 1998, vol. 120, pp. 6909-6919.

(Continued)

*Primary Examiner* — Antonio Galisteo Gonzalez
(74) *Attorney, Agent, or Firm* — Fay Sharpe LLP

(57) ABSTRACT

An object of the present invention is to provide novel double-stranded RNA having an RNA interference effect, in which the cellular uptake and the resistance to enzymatic degradation are improved, without reducing the RNA interference effect.
The cellular uptake and the resistance to enzymatic degradation of a complex of a polysaccharide having a β-1,3-glucan skeleton and double-stranded RNA can be significantly improved while maintaining the RNA interference effect, by fulfilling the following conditions (i) to (iii): (i) the double-stranded RNA has a sense strand consisting of a base sequence complementary to a target sequence in a target gene and an antisense strand containing a base sequence complementary to the sense strand, and the double-stranded RNA can inhibit expression of the target gene; (ii) the double-stranded RNA has a single-stranded polydeoxyadenine bound directly or via a linker to the end of at least one of the sense strand and the antisense strand; and (iii) the polysaccharide and the single-stranded polydeoxyadenine form a complex.

7 Claims, 11 Drawing Sheets
Specification includes a Sequence Listing.

(56) References Cited

OTHER PUBLICATIONS

Janet A. Willment et al., "Characterization of the Human β-Glucan Receptor and Its Alternatively Spliced Isoforms*", The Journal of Biological Chemisry, vol. 276, No. 27, Issue of Nov. 23, 2001, pp. 43818-43823.
Polymer Preprints, Japan, vol. 49, No. 13, 2000, pp. 4054-4055, including English translation of Polymer Preprints, 5 pages.
Dong-Ho Kim et al., "Synthetic dsRNA Dicer substrates enhance RNAi potency and efficacy", Nature Biotechnology, vol. 23, No. 2, Feb. 2005, pp. 222-226.
International Search Report dated Feb. 10, 2009 in International Application No. PCT/JP2008/073125.
European Official Communication dated Aug. 20, 2012, corresponding with European Patent Application No. 08862702.1.
J. Soutschek et al., "Therapeutic silencing of an endogenous gene by systemic administration of modified siRNAs", Nature, International Weekly Journal of Science, vol. 432, No. 7014, Nov. 11, 2004, pp. 173-178.
Sun Hwa Kim et al., "PEG conjugated VEGF siRNA for anti-angiogenic gene therapy", Journal of Controlled Release, vol. 116, No. 2, Nov. 28, 2006, pp. 123-129.
M. Grzelinski et al., "RNA interference-medicated gene silencing of pleiorophin through polyethylenimine-complexed small interfering RNAs in vivo exerts antitumoral effects in glioblastoma xenografts", Human Gene Therapy, vol. 17, No. 7, Jul. 15, 2006, pp. 751-766.
H. Katas et al., "Development and characterisation of chitosan nanoparticles for siRNA delivery", Journal of Controlled Release, vol. 115, No. 2, Oct. 10, 2006, pp. 216-225.
European Official Communication dated Dec. 9, 2013, corresponding with European Patent Application No. 08862702.1.

* cited by examiner

A. Modified SPGs

SPG 
SPG1 : SPG (Unmodified)
SPG2 : Peptide R8-Modified SPG
SPG3 : Peptide tat-Modified SPG
SPG4 : Peptide RGD-Modified PSG
SPG5 : Spermine-Modified SPG
SPG6 : PEG-Modified SPG B. Double-Stranded Oligonucleotides 21s/21as (21siRNA)

27s/27as (27dsRNA)

pA40-27R1/27as pA40-27R2/27as pA40-27R1/27as/SPG
(SPG =
SPG1~SPG6)

pA40-27R2/27as/SPG
(SPG =
SPG1~SPG6)

Length of Double Strand (bp) Measured by AFM and

COMPLEX OF POLYSACCHARIDE AND DOUBLE-STRANDED RNA

CROSS-REFERENCE TO RELATED APPLICATIONS

This application is a National Phase Entry of International Application No. PCT/JP2008/073125, filed Dec. 18, 2008, which claims foreign priority to Japanese Patent Application No. 2007-3265104, filed Dec. 18, 2007. The complete disclosures of the referenced applications, including sequence listings, are incorporated herein by reference.

SEQUENCE LISTING

The instant application contains a Sequence Listing which has been submitted via EFS-Web and is hereby incorporated by reference in its entirety. Said ASCII copy, created on Jun. 28, 2010, is named 81569817.txt and is 6,305 bytes in size.

TECHNICAL FIELD

The present invention relates to a polysaccharide/double-stranded RNA complex, which is a complex of double-stranded RNA capable of inhibiting expression of a target gene and a polysaccharide having a β-1,3-glucan skeleton, wherein the complex can efficiently provide RNA interference effect mediated by the action of the double-strand RNA; and further, by binding a functional molecule to the polysaccharide, the complex can also demonstrate a useful function mediated by the action of the functional molecule.

BACKGROUND ART

In recent years, an RNA interference (RNAi) method using a 21-base-long, short double-stranded RNA (small interfering RNA: siRNA) has been attracting attention. According to this RNAi method, an approximately 100-base-pair-long double-stranded RNA is transfected into a cell so as to be digested into about 20- to about 25-base-pair-long double-stranded RNA fragments by the action of Dicer in the cytoplasm. The RNA fragments are then combined with a plurality of proteins to form an RNA/protein complex (this complex is referred to as an "RISC": RNA-Induced Silencing Complex), which binds to a homologous region of mRNA produced from the target gene and thereby potently inhibits gene expression. The principal method used today utilizes a chemically synthesized 21-base-long double-stranded RNA having a dangling end of two bases on the 3'-end. A recent report by J. Rossi et al. revealed that a 27-base-pair-long double-stranded RNA has an RNA interference effect that is about 100 times greater than that of a 21-base-long siRNA (see Non-Patent Document 1). This great effect is considered to be achieved for the following reason: after a 27-base-pair-long RNA is cleaved with an RNase III-like enzyme, Dicer, into a 21-base-long siRNA, the siRNA is recognized as is by the protein complex RISC, allowing siRNA effects to be exhibited with high efficiency.

According to the above RNA interference method using a synthetic RNA, sample preparation is relatively easy and handling is simple. Therefore, the method has been attracting a great deal of attention in the field of biotechnology business, as well as in the life science field.

However, even this excellent RNA interference method is unsatisfactory in terms of intracellular stability, cellular uptake, intracellular localization, gene expression-inhibiting effect, target specificity, etc.; accordingly, further improvement in these aspects has been desired. Recently, various chemically modified siRNAs have been produced to provide synthetic siRNAs with enhanced nuclease resistance and highly active RNA interference effects. For example, to enhance the resistance to exonuclease digestion, siRNAs, whose end is modified with an amino group or a thiol group etc. or is modified to form an abasic site etc., have been synthesized. However, it has been reported that although terminal modification of a double-stranded RNA having an RNA interference effect may enhance nuclease resistance and increase the transfection rate, it also greatly reduces the RNA interference effect. It was thus impossible in the prior art to provide an improved double-stranded RNA having an RNA interference effect, which has an enhanced nuclease resistance and cell transfection rate as well as a further increased RNA interference effect.

β-1,3-glucan is a polysaccharide that is actually used in the form of a clinical intramuscular injectable formulation. It has long been known that natural β-1,3-glucan exists as a triple helix (see Non-Patent Document 2). In vivo safety of this polysaccharide has also been confirmed, and β-1,3-glucan has been used as an intramuscular injectable formulation for about 20 years (see Non-Patent Document 3). It has also been reported that β-1,3-glucan has drug delivery ability, and a covalent bond formed between β-1,3-glucan and the drug enables a drug to be delivered to a target site (see Patent Document 1).

Natural β-1,3-glucan is known to exist as a triple helix. Further, it has been revealed that when this polysaccharide is dissolved in a polar solvent so as to be disintegrated into independent single strands, then single-stranded nucleic acid is added, and the solvent is replaced with water (a renaturation process), a triple helical complex consisting of one strand of nucleic acid and two strands of the polysaccharide is formed (see Non-Patent Document 4). It is believed that the nucleic acid and the polysaccharide in such a triple helical complex are complexed principally by hydrogen bonds.

In recent years, the present inventors further revealed that the delivery of a gene can be accomplished by forming a complex comprising β-1,3-glucan and the gene (see Patent Document 2). Further, a method for transfecting nucleic acid using β-1,3-glucan having a cell membrane-permeable functional group and a lipid membrane disrupting functional group was reported (see Patent Document 3). However, these publications only disclose methods for transfecting a single-stranded nucleic acid into cells, and are silent as to double-stranded siRNA etc. Patent Document 4 discloses a method for transfecting a double-stranded DNA having genetic information into a target cell using β-1,3-glucan. However, putting this method to practical use appears to be difficult due to its low transfection efficiency.

Thus, when β-1,3-glucan is merely complexed with a double-stranded RNA having an RNA interference effect, a triple helical structure is not formed, or a triple helix is formed, but the double-stranded RNA may no longer be double-stranded; accordingly, the desired effect cannot be expected to be produced. Further, a double-stranded RNA having an RNA interference effect is different from a DNA having genetic information in the mechanism of action required in cells. Intracellular complexing of the double-stranded RNA with RISC, and binding to a homologous region of mRNA produced from the target gene are important to provide the RNA interference effect. Therefore, even if the method disclosed in Patent Document 4 is applied to a double-stranded RNA having an RNA interference effect, a low RNA transfection efficiency, as in the case of the DNA, or a great reduction of the RNA interference effect in cells is expected.

Patent Document 1: WO 96/014873 pamphlet
Patent Document 2: WO 01/34207 pamphlet
Patent Document 3: Japanese Unexamined Patent Publication No. 2006-69913
Patent Document 4: Japanese Unexamined Patent Publication No. 2005-204612
Non-Patent Document 1: J. Rossi et al., Nature Biotech., 23, 222-226 (2005)
Non-Patent Document 2: Theresa M. et al., J. Am. Chem. Soc., 120, 6909 (1998)
Non-Patent Document 3: Hasegawa, Oncology and Chemotherapy, 8, 225 (1992)
Non-Patent Document 4: Kazuo Sakurai, Polym. Preprints. Jpn., volume 49, page 4054, 2000

DISCLOSURE OF THE INVENTION

Technical Object

Accordingly, a main object of the present invention is to improve the cellular uptake and the resistance to enzymatic degradation of double-stranded RNA having an RNA interference effect, without reducing the RNA interference effect.

Technical Solution

The present inventors conducted extensive studies to achieve the above object, and found that it is possible to significantly improve the cellular uptake and the resistance to enzymatic degradation of a complex of a polysaccharide having a β-1,3-glucan skeleton and double-stranded RNA, while maintaining the RNA interference effect, by fulfilling the following conditions (i) to (iii):
(i) the double-stranded RNA has a sense strand consisting of a base sequence complementary to a target sequence in a target gene and an antisense strand containing a base sequence complementary to the sense strand, and the double-stranded RNA can inhibit expression of the target gene;
(ii) the double-stranded RNA has a single-stranded polydeoxyadenine bound directly or via a linker to the end of at least one of the sense strand and the antisense strand; and
(iii) the polysaccharide and the single-stranded polydeoxyadenine form a complex.

The present invention is accomplished by making further improvements based on the above findings.

In other words, the present invention provides a polysaccharide/double-stranded RNA complex and its production process, as described below.

Item 1. A polysaccharide/double-stranded RNA complex, wherein the polysaccharide has a β-1,3-glucan skeleton; the double-stranded RNA has a sense strand RNA consisting of a base sequence complementary to a target sequence in a target gene and an antisense strand RNA containing a base sequence complementary to the sense strand RNA, and the double-stranded RNA can inhibit expression of the target gene;
the double-stranded RNA has a single-stranded polydeoxyadenine bound directly or via a linker to the end of at least one of the sense strand RNA and the antisense strand; and
the polysaccharide and the single-stranded polydeoxyadenine form a complex.

Item 2. The polysaccharide/double-stranded RNA complex as defined in Item 1, wherein the single-stranded polydeoxyadenine and the two polysaccharides form a triple helical structure by complexing the single-stranded polydeoxyadenine with two such polysaccharides.

Item 3. The polysaccharide/double-stranded RNA complex as defined in Item 1, wherein the sense strand RNA consists of 15 to 50 ribonucleotides, and the antisense strand RNA consists of the same number of ribonucleotides as that of the sense strand RNA.

Item 4. The polysaccharide/double-stranded RNA complex as defined in Item 1, wherein the sense strand RNA consists of 21 ribonucleotides, and the antisense strand RNA consists of the same number of ribonucleotides as that of the sense strand RNA.

Item 5. The polysaccharide/double-stranded RNA complex as defined in Item 1, wherein the sense strand RNA consists of 27 ribonucleotides, and the antisense strand RNA consists of the same number of ribonucleotides as that of the sense strand RNA.

Item 6. The polysaccharide/double-stranded RNA complex as defined in Item 1, wherein the single-stranded polydeoxyadenine consists of 20 to 100 deoxyadenines (SEQ ID NO: 13).

Item 7. The polysaccharide/double-stranded RNA complex as defined in Item 1, wherein the single-stranded polydeoxyadenine is bound directly or via a linker to the 5' and/or 3' end of the sense strand RNA or antisense strand RNA.

Item 8. The polysaccharide/double-stranded RNA complex as defined in Item 1, wherein the polysaccharide is at least one member selected from the group consisting of schizophyllan, curdlan, lentinan, pachyman, grifolan, and scleroglucan.

Item 9. The polysaccharide/double-stranded RNA complex as defined in Item 1, wherein the polysaccharide is a β-1,3-glucan to which a functional molecule is bound.

Item 10. The polysaccharide/double-stranded RNA complex as defined in Item 9, wherein the functional molecule is a cell membrane-permeable molecule or a molecule capable of providing resistance to enzymatic degradation to double-stranded RNA.

Item 11. The polysaccharide/double-stranded RNA complex as defined in Item 9, wherein the functional molecule is a peptide, cationic molecule, or polyethyleneglycol.

Item 12. The polysaccharide/double-stranded RNA complex as defined in Item 1, wherein a target gene of the double-stranded RNA is endogenous to a cell having a receptor that binds to the polysaccharide.

Item 13. The polysaccharide/double-stranded RNA complex as defined in Item 1, wherein the cell is a cell that expresses Dectin-1 on the membrane surface of the cell.

Item 14. The polysaccharide/double-stranded RNA complex as defined in Item 1, wherein the complex is delivered into a cell through a signal induced by the binding to the Dectin-1.

Item 15. The polysaccharide/double-stranded RNA complex as defined in Item 1, wherein the target gene is a factor involved in the onset of a clinical condition or the worsening of a symptom by causing overproduction of a transcriptional product from the target gene through an external stimulus, etc.; or a factor having a region where the target gene is mutated and whose transcriptional product is directly involved in the pathogenesis.

Item 16. The polysaccharide/double-stranded RNA complex as defined in Item 15, wherein the product transcribed in excess from the target gene is a factor that induces inflammation.

Item 17. The polysaccharide/double-stranded RNA complex according to Item 15, wherein the product transcribed in excess from the target gene is at least one selected from the group consisting of TNFα, interleukin, and MIF.

Item 18. The polysaccharide/double-stranded RNA complex as defined in Item 15, wherein the product transcribed in excess from the target gene is a factor that turns on and off the intracellular activity.

Item 19. The polysaccharide/double-stranded RNA complex as defined in Item 15, wherein the product transcribed in excess from the target gene is a cell surface receptor, and is also a factor that acts on the onset or worsening of medical conditions through the cell surface receptor.

Item 20. The polysaccharide/double-stranded RNA complex as defined in Item 1, wherein the target gene is a factor having a mutated region and thereby a transcriptional product thereof causes a loss of normal cell function or accumulates as a cytotoxic substance, thus inducing the onset/worsening of clinical conditions such as inflammation and cell death.

Item 21. A process of producing the polysaccharide/double-stranded RNA complex as defined in Item 1,
whereinthe double-stranded RNA has a sense strand RNA consisting of a base sequence complementary to a target sequence in a target gene and an antisense strand RNA containing a base sequence complementary to the sense strand RNA, and can inhibit expression of the target gene;
the process comprising:
a step of mixing a polysaccharide having a β-1,3-glucan skeleton in a ratio of from 1 to 6 mol to 1 mol of the polynucleotide-binding double-stranded RNA having a single-stranded polydeoxyadenine bound directly or via a linker to the end of at least one of the sense strand and antisense strand, thus forming a complex of the single-stranded polydeoxyadenine and the polysaccharide.

Item 22. A use of polysaccharide/double-stranded RNA complex to inhibit expression of a target gene in vitro or ex vivo,
wherein the polysaccharide has a β-1,3-glucan skeleton;
the polysaccharide/double-stranded RNA complex contains double-stranded RNA having a sense strand RNA consisting of a base sequence complementary to a target sequence in a target gene and an antisense strand RNA containing a base sequence complementary to the sense strand RNA, and capable of inhibiting expression of the target gene;
the double-stranded RNA has a single-stranded polydeoxyadenine bound directly or via a linker to the end of at least one of the sense strand RNA and antisense strand; and
the polysaccharide and the single-stranded polydeoxyadenine form a complex.

Item 23. A method of inhibiting expression of a target gene in a cell, comprising:
a step of introducing a polysaccharide having a β-1,3-glucan skeleton/double-stranded RNA complex into a cell;
wherein the polysaccharide/double-stranded RNA complex contains double-stranded RNA having a sense strand RNA consisting of a base sequence complementary to a target sequence in a target gene and an antisense strand RNA containing a base sequence complementary to the sense strand RNA, and capable of inhibiting expression of the target gene;
the double-stranded RNA has a single-stranded polydeoxyadenine bound directly or via a linker to at least one end of the sense strand and antisense strand; and
the polysaccharide and the single-stranded polydeoxyadenine form a complex.

Advantageous Effects

The polysaccharide/double-stranded RNA complex of the present invention has excellent cellular uptake and resistance to enzymatic degradation, while maintaining the RNA interference effect mediated by double-stranded RNA, and thus the practical value of the polysaccharide/double-stranded RNA complex is improved compared to the conventional double-stranded RNA molecule that produces the RNA interference effect. Therefore, the polysaccharide/double-stranded RNA complex of the present invention is applicable as a gene drug effective in the treatment of diseases such as cancer and AIDS.

Further, various functional molecules such as cell membrane-permeable molecules and other molecules capable of providing resistance to enzymatic degradation can be bound to the polysaccharide of the polysaccharide/double-stranded RNA complex of the present invention. Thus, the complex can also be provided with useful effects mediated by the functional molecules, allowing a variety of molecular designs and increasing clinical usefulness.

Further, when the double-stranded RNA forming the polysaccharide/double-stranded RNA complex of the present invention comprises a sense strand RNA consisting of 27 ribonucleotides and an antisense strand RNA consisting of 27 ribonucleotides fully complementary to the sense strand RNA, the above-described effects of the present invention can be further effectively achieved. Although this should not be interpreted in a limited manner, the reason for the further effective effects is considered as follows: After the polysaccharide/double-stranded RNA complex having double-stranded RNA in the above-described structure is introduced into a cell, the 27-base-long double-stranded RNA is efficiently converted to 21-base-long siRNA having a 2 base dangling end at the 3' end by the action of Dicer, so that the polysaccharide bound to the end of the 27-base-long double-stranded RNA via polydeoxyadenine is separated. In other words, although the polysaccharide plays an important role in improving the double-stranded RNA in terms of the cellular uptake, the nuclease resistance, and the like, the polysaccharide has no adverse effect on the RNA interference reaction. Generally, modified RNA interference molecules are reported to have a reduced RNA interference effect. However, in the case of the polysaccharide/double-stranded RNA complex of the present invention, the polysaccharide is separated by the action of Dicer as described above, so that the RNA interference effect is not impaired. Therefore, the polysaccharide/double-stranded RNA complex having double-stranded RNA with the above-described structure can effectively express its inherent RNA interference effect, while improving the cellular uptake, the nuclease resistance, and the like.

BEST MODE FOR CARRYING OUT THE INVENTION

The polysaccharide/double-stranded RNA complex of the present invention contains double-stranded RNA that produces the RNA interference effect. The double-stranded RNA is formed by the hybridization of sense strand RNA consisting of a base sequence complementary to a target sequence in a target gene and antisense strand RNA containing a base sequence complementary to the sense strand, and is capable of inhibiting expression of the target gene. The "sense strand RNA containing a base sequence complementary to a target sequence" herein refers a complementary sequence that matches the target sequence 100%.

The "target gene" herein refers to a gene whose expression is to be inhibited by the RNA interference effect. With the polysaccharide/double-stranded RNA complex of the present invention, the target gene is not particularly limited, and can be suitably selected based on the application of the polysaccharide/double-stranded RNA complex.

In the present invention, it is desirable that the target gene is present in a cell expressing a receptor on the cell surface, the receptor being capable of binding to a polysaccharide. A preferable example of such a cell is one that expresses Dectin-1, which is a receptor of β-glucan. The polysaccharide having a β-1,3-glucan skeleton is delivered into a cell through a signal induced by the binding to Dectin-1 on the cell surface.

Although the target gene of the present invention is not particularly limited, in view of use for medical applications, a gene that is involved in clinical conditions and whose expression is desired to be inhibited is preferred. Examples of the target gene include (a) genes that encode a factor involved in the onset of a clinical condition or the worsening of a symptom by causing overproduction of a transcriptional product from the genes through an external stimulus, etc., and (b) genes that encode a factor having a region where the target gene is mutated and whose transcript is directly involved in the onset of a disease.

Examples of the above-described target genes include genes that encode a factor that induces inflammation such as cytokines, for example, TNFα, interleukin, MIF, and other like.

The target genes (a) may also be genes that encode a factor that turns on and off the intracellular activity. Examples of such genes include protein kinases (for example, Raf, MEK, Jak2, etc.), transcription factors (for example, Stat5, etc.), and the like.

Examples of the target genes (a) further include the target genes that encode a cell surface receptor and also encode a factor that acts on the onset or worsening of medical conditions through the cell surface receptor. Examples of such genes include ones that encode TNFR (tumor necrosis factor receptor), PDGFR (platelet-derived growth factor receptor), interleukin receptor, and the like.

The target genes (b) indicate genes that encode a factor having a region where the target gene is mutated and thereby a transcript thereof causes a loss of normal cell function or accumulates as a cytotoxic substance, thus inducing the onset/worsening of clinical conditions such as inflammation and cell death. Examples of such genes include Jak2 mutation V617F, ATN1 mutation CAG repeat, TTR mutation V30M, KT14 mutation R125C, and the like.

The target sequence in the target gene is not particularly limited insofar as the expression of the gene can be inhibited by the RNA interference effect. The target sequence can be suitably determined according to a known method; specifically, an NCBI BLAST search or the like can be used. For example, the target sequence may be a region consisting of 19 to 30 bases following the bases "AA" in the exon region 50 to 100 bases downstream of the start codon of the coding region (ORF) of the target gene, and having a GC content of about 50%. It is experientially known in this field that excellent RNA interference effect can be obtained using a strand complementary to such a target sequence. For example, the target sequence can be determined according to the instructions of IDT (Integrated DNA Technologies, Inc.; Dicer Substrate RNAi Design). A recent report revealed that double-stranded RNA having high RNA interference effect can be produced by designing double-stranded RNA which has: (i) an A/U pair at the 5' end of the antisense strand RNA; (ii) a G/C pair at the 5' end of the sense strand RNA; and (iii) about five A/U pairs at the 5' end side of the antisense strand RNA; and (iv) does not have nine or more G/C pairs in the double strand (Ui-Tei et al., Nucleic Acids Res., 32, 936-948 (2004)).

The number of ribonucleotides constituting the sense strand RNA is not particularly limited insofar as the RNA interference effect can be expressed. For example, the number is 15 to 50, 19 to 30, preferably 21 to 27, further preferably 21 or 27.

Further, the antisense strand RNA is an RNA capable of forming a double-strand by hybridizing with the sense strand RNA. In other words, the antisense strand RNA is an RNA containing a nucleotide sequence complementary to the sense strand RNA. Although the antisense strand RNA may not necessarily have a sequence complementary to the entire length of the sense strand RNA, it is preferred that the antisense strand RNA has a sequence complementary to a region of 15 bases or longer, preferably 19 bases or longer, in the sense strand RNA.

The number of ribonucleotides constituting the antisense strand is also not particularly limited. For example, the number is 15 to 50, 19 to 30, preferably 21 to 27, further preferably 21 or 27. Note that, although the sense strand and the antisense strand may have different numbers of ribonucleotides, it is preferred that they have the same number of ribonucleotides.

Further, the sense strand RNA and the antisense strand may be hybridized into a double strand, having a dangling end (overhang) at one or both of the 5' end side of the sense strand RNA (i.e., the 3' end side of the antisense strand) and the 3' end side of the sense strand RNA (i.e., the 5' end side of the antisense strand). Additionally, when the sense strand RNA and the antisense strand both consist of the same number of ribonucleotides, they may be hybridized into a double strand in which both of the 5' end side of the sense strand RNA (i.e., the 3' end side of the antisense strand) and the 3' end side of the sense strand RNA (i.e., the 5' end side of the antisense strand) are blunt ends; in other words, the sense strand RNA and the antisense strand may be fully complementary hybridized. The "dangling end" used herein refers to a terminal structure of a double-strand formed by the hybridization of the sense strand RNA and the antisense strand, wherein an end region of the sense strand RNA or antisense strand is single stranded because a pairing nucleotide is not present. Additionally, the "blunt end" refers to a terminal structure of a double-strand formed by the hybridization of the sense strand RNA and the antisense strand, wherein an end region of the sense strand RNA and its pairing end region of the antisense strand are completely paired with each other, without dangling ends.

A preferable embodiment of the double-stranded RNA constituting the polysaccharide/double-stranded RNA complex of the present invention is one in which the sense strand RNA consists of 27 ribonucleotides, and the antisense strand RNA also consists of 27 ribonucleotides fully complementary to the sense strand RNA. In other words, when the double-stranded RNA has such a structure, both of the 5' and 3' ends are blunt-ended.

Another example of the double-stranded RNA constituting the polysaccharide/double-stranded RNA complex of the present invention includes one in which the sense strand RNA and the antisense strand RNA both consist of 21 ribonucleotides, and a dangling end consisting of 2 ribonucleotides is formed at the 5' end of the sense strand RNA and the 5' end of the antisense strand RNA. In other words, in the case of the double-stranded RNA as described above, a sequence of 1 to 19 ribonucleotides from the 3' end side of the antisense strand RNA is complementary to a sequence of 3 to 21 ribonucleotides from the 5' end side of the sense strand RNA.

The double-stranded RNA constituting the polysaccharide/double-stranded RNA complex of the present invention has a single-stranded polydeoxyadenine bound directly or via a linker to at least one of the four ends of the sense strand and the antisense strand. In other words, a single-stranded polydeoxyadenine is bound to at least one of the following ends: the 5' end of the sense strand RNA, the 3' end of the sense strand, the 5' end of the antisense strand, and the 3' end of the antisense strand. The number of bindings of the single-stranded polydeoxyadenines is not particularly limited. In terms of efficient production of the RNA interference effect, the number is preferably 1 to 3, further preferably 1 or 2, and particularly preferably 1.

In the present invention, it is preferred that the number of bindings of the single-stranded polydeoxyadenines to the double-stranded RNA is one, and that the single-stranded polydeoxyadenines is bound to the 5' end of the sense strand. When the single-stranded polydeoxyadenine is bound to only the 5' end of the sense strand as described above, the RNA interference effect mediated by the double-stranded RNA can be significant. Further, when the single-stranded polydeoxyadenine is bound to only the 5' end of the sense strand, and when both the sense strand and the antisense strand of the double-stranded RNA consist of 27 nucleotides, a further enhanced expression of the RNA interference effect can be induced.

Further, when the sense strand RNA and the antisense strand RNA both consist of 21 ribonucleotides, the single-stranded polydeoxyadenine may be bound to either the 5' end or the 3' end of the sense strand or antisense strand, and a high RNA interference effect can be demonstrated. d The number of deoxyadenines constituting the single-stranded polydeoxyadenine is not particularly limited insofar as a complex can be formed between the deoxyadenines and a polysaccharide having a β-1,3-glucan skeleton described below. For example, the number of deoxyadenines is 10 to 100 (SEQ ID NO: 14), preferably 20 to 100, more preferably 20 to 80, further preferably 40 to 60.

The single-stranded polydeoxyadenine forms a suitable complex with a polysaccharide having a β-1,3-glucan skeleton, and a polysaccharide/double-stranded RNA complex thus obtained has a high resistance to enzymatic degradation.

The single-stranded polydeoxyadenine may be bound to a terminal ribonucleotide of the sense strand RNA and/or antisense strand RNA of the double-stranded RNA, directly or via a linker. The latter, i.e., the binding via a linker, is preferred.

Specifically, in order to directly bind the single-stranded polydeoxyadenine to the 5' end of the RNA strand, a 5' carbon atom of the ribonucleotide at the 5' end of the RNA strand may be bound by an ester linkage to a phosphate residue, which is bound by an ester linkage to a 3' carbon atom at the 3' end of the single-stranded polydeoxyadenine. Further, in order to directly bind the single-stranded polydeoxyadenine to the 3' end of the RNA strand, a phosphate residue bound by an ester linkage to a 3' carbon atom of the ribonucleotide at the 3' end of the RNA strand may be bound by an ester linkage to a 5' carbon atom at the 5' end of the single-stranded polydeoxyadenine.

Further, when the single-stranded polydeoxyadenine is bound via a linker to the sense strand RNA and/or antisense strand RNA of the double-stranded RNA, a bifunctional linker, for example, may be used as the linker.

The bifunctional linker used herein may not be particularly limited insofar as the linker contains two functional groups. Examples of linkers that can be used include N-succinimidyl=3-(2-pyridyldithio)propionate, N-4-maleimidobutyric acid, S-(2-pyridyldithio)cysteamine, iodoacetoxysuccinimide, N-(4-maleimidobutyryloxy)succinimide, N-[5-(3'-maleimide propylamide)-1-carboxypentyl]iminodiacetic acid, N-succinimidyl-3-maleimidopropionate, and the like.

In addition to those listed above, linkers of the following structures may also be used as the bifunctional linker.

[Chem. 1]

 (L-1)

 (L-2)

 (L-3)

 (L-4)

 (L-5)

 (L-6)

 (L-7)

 (L-8)

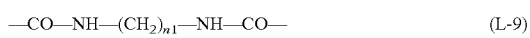 (L-9)

 (L-10)

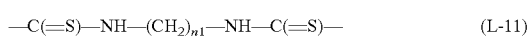 (L-11)

 (L-12)

 (L-13)

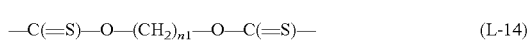 (L-14)

 (L-15)

 (L-16)

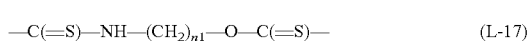 (L-17)

 (L-18)

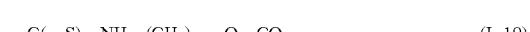 (L-19)

 (L-20)

 (L-21)

 (L-22)

 (L-23)

 (L-24)

 (L-25)

In the above General Formulae (L-4) to (L-21), n1 is an integer of from 1 to 40, preferably from 2 to 20, further preferably from 2 to 12.

Further, in General Formulae (L-22) to (L-24), n2 is an integer of from 1 to 20, preferably from 1 to 10, further preferably from 1 to 6.

Furthermore, in General Formula (L-25), each of n3 and n4, which are the same or different, is an integer of from 1 to 20, preferably from 1 to 10, further preferably from 1 to 6.

With regard to each of the linkers shown in General Formulae (L-4) to (L-25), the single-stranded polydeoxyadenine may be bound to either the right or left side of the linker. A preferable structure is such that the single-stranded polydeoxyadenine is bound to the left side, and an end of the sense strand RNA and/or antisense strand RNA of the double-stranded RNA is bound to the right side.

Additionally, the linker binding site in the terminal ribonucleotide of the sense strand RNA and/or antisense strand RNA of the double-stranded RNA is not particularly limited. For example, the linker may be substituted with a hydrogen atom constituting the phosphate residue of the terminal ribonucleotide of the sense strand RNA and/or antisense strand RNA and thereby bound thereto, or the linker may be substituted with a hydrogen atom constituting a hydroxyl group of the terminal ribonucleotide and thereby bound thereto. Further, the linker binding site in the terminal deoxyribonucleotide of the single-stranded polydeoxyadenine is also not particularly limited. For example, the linker may be substituted with a hydrogen atom constituting the phosphate residue of the terminal deoxyribonucleotide of the single-stranded polydeoxyadenine and thereby bound thereto, or the linker may be substituted with a hydrogen atom constituting a hydroxyl group of the terminal deoxyribonucleotide and thereby bound thereto.

The polysaccharide/double-stranded RNA complex of the present invention contains a polysaccharide having a β-1,3-glucan skeleton as a role to perform desired functions other than the RNA interference effect.

β-1,3-glucan is a polysaccharide to which glucose is bound by β1→4-glucoside bonds. Various β-1,3-glucans are known in which the ratio of the number of glucose residues in the side chains to the number of glucose residues in the main chain (hereinbelow abbreviated as "side chain ratio") differs. Although the polysaccharide used in the present invention is not particularly limited insofar as it has a β-1,3-glucan skeleton, a polysaccharide having a β-1,3-glucan skeleton with a higher side chain ratio is preferably used in view of the fact that such a polysaccharide can easily form a complex with the single-stranded polydeoxyadenine and can further improve the rate of cell introduction of the polysaccharide/double-stranded RNA complex of the present invention.

Specific examples of the polysaccharide used in the polysaccharide/double-stranded RNA complex of the present invention include schizophyllan, curdlan, lentinan, pachyman, grifolan, scleroglucan, and the like. Of these, schizophyllan is a preferable polysaccharide in the present invention because it can further significantly improve the cellular uptake and the resistance to enzymatic degradation.

The molecular weight of the polysaccharide used in the polysaccharide/double-stranded RNA complex of the present invention is not particularly limited. It may be suitably determined according to the type of the polysaccharide used, the chain length of the single-stranded polydeoxyadenine, and the like. Specifically, the molecular weight of the polysaccharide is usually 25,000 to 2,500,000, preferably 25,000 to 150,000.

The polysaccharide/double-stranded RNA complex of the present invention is formed as the single-stranded polydeoxyadenine bound to the double-stranded RNA forms a complex with the polysaccharide. The complex structure between the single-stranded polydeoxyadenine and the polysaccharide is not particularly limited. Usually, a triple helical structure wherein the single-stranded polydeoxyadenine forms a complex with two such polysaccharides is preferred. The triple helical structure as described above can be formed specifically according to the following processes: Under natural conditions or in water, a polysaccharide having a β-1,3-glucan skeleton has a triple helical structure. This polysaccharide is dissolved in a polar solvent such as DMSO (dimethyl sulfoxide) or the like into single strands, to which is then added double-stranded RNA having a single-stranded polydeoxyadenine bound thereto, and the solvent is replaced by water (a renaturation process), thereby forming a complex structure in the triple helical form (association structure) comprising a single strand of polynucleotide bound to double-stranded RNA and two polysaccharides. Such a complex of polynucleotide and polysaccharides is considered to be formed mainly via hydrogen bonding and hydrophobic interaction.

Further, the polysaccharide contained in the polysaccharide/double-stranded RNA complex of the present invention may have a functional molecule bound thereto. By using a polysaccharide to which a functional molecule is bound as described above, a useful function mediated by the functional molecule can be provided to the polysaccharide/double-stranded RNA complex of the present invention. Specific examples of such functional molecules include peptides, proteins, sugars, amino acids, DNA, RNA, low-molecular organic/inorganic materials, cholesterols, dendrimers, lipids, high-molecular materials, and the like.

Examples of peptides include peptides comprising 30 to 40, preferably 6 to 30, further preferably 8 to 25 amino acids. Specific examples thereof include cell membrane-permeable peptides (octaarginine (R8) ("R8" disclosed as SEQ ID NO: 20), penetratin, etc.), nuclear localization signal peptide sequences (HIV-1Tat, SV40 T antigen, etc.), nuclear exporting signal peptides (HIV-1Rev, MAPKK, etc.), cellular membrane fusion peptides (gp41, viral fusion peptides, etc.). Of these, R8 (SEQ ID NO: 20) is preferably used in the present invention. R8 (SEQ ID NO: 20) has an action of promoting cell introduction. Use of a polysaccharide to which R8 (SEQ ID NO: 20) is bound can provide an advantage in that the polysaccharide/double-stranded RNA complex can be further efficiently introduced into a cell.

Proteins present in vivo, proteins having medicinal properties, proteins having molecular recognition properties, etc. can be used as the above-described proteins. Examples of such proteins include exporting/importing proteins, fibronectins, avidins, antibodies, and the like.

Examples of sugars include monosaccharides such as glucose, galactose, glucosamine, galactosamine, etc.; oligosaccharides or polysaccharides in which these monosaccharides are combined in any manner; and the like.

Examples of low-molecular organic/inorganic materials include cationic molecules such as spermine, spermidine, etc.; fluorescent materials such as FITC, Alexa, Cy3, Cy5, etc.; biotins; quantum dots; gold fine particles; and the like.

Examples of dendrimers include polyamidoamine dendrimers and the like.

Examples of lipids include linoleic acids, DOPE (1,2-Dioleoyl-sn-glycero-3-phosphoethanolamine), and the like.

Examples of high-molecular materials include polyethyleneglycols, polyethylenimines, and the like.

Of the functional molecules, peptides, cationic molecules, and polyethyleneglycols are preferred, and peptides are particularly preferred. Additionally, of the functional molecules, molecules having cell membrane permeability (cell membrane-permeable molecule) and molecules capable of providing the resistance to enzymatic degradation to double-stranded RNA are preferred. Of the functional molecules, examples of cell membrane-permeable molecules include peptides and the like, and examples of molecules capable of providing the resistance to enzymatic degradation to double-stranded RNA include polyethyleneglycols.

A functional molecule may be bound to the polysaccharide by binding the functional molecule to a side chain of the polysaccharide directly or via a linker. Although various reactions are possible as methods for binding a functional molecule to a side chain of the polysaccharide, a method of selectively introducing a functional molecule into a side chain without affecting the glycosidic bond in the main chain is preferably selected. The following method is an example of such a method. Specifically, first, glucose residues having 1,6-glucopyranoside bonds, which are branched from the main chain of schizophyllan or the like, are oxidized using an oxidant such as sodium periodate, resulting in the opening of the ring and the formation of an aldehyde. Next, the aldehyde group is reductively aminated in the presence of a reducing agent such as sodium borohydride or the like, using the amino group of an amino group-containing functional molecule or the amino group of a functional molecule bound to an amino group-containing linker. Thereby, a polysaccharide to which a functional molecule is bound can be synthesized.

Other methods include the following, for example: First, glucose residues having 1,6-glucopyranoside bonds, which are branched from the main chain of schizophyllan or the like, are oxidized using an oxidant such as sodium periodate, resulting in the opening of the ring and the formation of an aldehyde. Next, after the aldehyde group is oxidized to a carboxylic acid with sodium chlorite, the carboxylic acid is subjected to a condensation reaction with an amino group-containing functional molecule or a functional molecule bound to an amino group-containing linker, using diphenylphosphoryl azide. This method can likewise produce a target material.

When a functional molecule is bound to the polysaccharide, the functional molecule-to-polysaccharide binding ratio is, for example, 1 to 200, preferably 1 to 100, particularly preferably 1 to 50 functional molecules per 100 side chains of the polysaccharide. The functional molecule-to-polysaccharide binding ratio as described above can be adjusted by controlling the amount of oxidant such as sodium periodate to be added to the branched glucose residues.

When a functional molecule is bound to the polysaccharide, it is preferred that the functional molecule is bound to a side chain of the polysaccharide via a linker. The above-mentioned bifunctional linker is preferably used as such a linker.

Further, although the binding site of the polysaccharide to the functional molecule or a linker that binds the functional molecule is not particularly limited, it is preferred that the functional molecule or a linker that binds the functional molecule is substituted with a 1,2-diol moiety of glucose having 1,6-glucopyranoside bonds, which is branched from the main chain of β-1,3-glucan in the polysaccharide.

The polysaccharide/double-stranded RNA complex of the present invention can be prepared according to a known method. Specifically, a production method comprising the following (1) to (3) steps is described as an example: (1) preparing polynucleotide-binding double-stranded RNA to which the single-stranded polydeoxyadenine is bound directly or via a linker, according to a known method; (2) additionally, separately providing a polysaccharide having a β-1,3-glucan skeleton, or preparing a polysaccharide (modified polysaccharide) having a β-1,3-glucan skeleton to which a functional molecule is bound directly or via a linker; and then (3) forming a complex using the single-stranded polydeoxyadenine bound to the DNA-binding double-stranded RNA and the polysaccharide or the modified polysaccharide.

In Step (3) of the above-described method, it is preferred that the polynucleotide-binding double-stranded RNA and the polysaccharide or the modified polysaccharide are mixed in a molar ratio of 1:1 to 1:5, preferably 1:1.3 to 1:2 to form a complex of a single-stranded polydeoxyadenine region of the polynucleotide-binding double-stranded RNA and the polysaccharide or the modified polysaccharide. The polynucleotide-binding double-stranded RNA and the polysaccharide or the modified polysaccharide are exposed to complex formation conditions in the above-described molar ratio. This allows efficient interaction therebetween, improving the production efficiency of the polysaccharide/double-stranded RNA complex of the present invention.

The polysaccharide/double-stranded RNA complex of the present invention can be used as a drug to inhibit expression of a target gene because the complex can inhibit expression of a target gene in a cell through introduction into a cell. The amount and method of introduction of the polysaccharide/double-stranded RNA complex of the present invention into a cell are the same as those of the conventional siRNA. Note that, because the polysaccharide/double-stranded RNA complex of the present invention exhibits excellent intracellular transfer ability by itself, the complex can be introduced into a cell without using a conventional gene transfection reagent that has been used to transfect siRNA into a cell, or with reduced usage of a conventional gene transfection reagent. Note that the expression of a target gene can be inhibited by the polysaccharide/double-stranded RNA complex of the present invention in vivo, in vitro or ex vivo.

The present invention also provides a use of the above-described polysaccharide/double-stranded RNA complex for inhibiting expression of a target gene in a cell. Further, the present invention also provides a method of inhibiting expression of a target gene, using the above-described polysaccharide/double-stranded RNA complex. The application and the like of the polysaccharide/double-stranded RNA complex in the above-mentioned use and method are as described above.

DESCRIPTION OF EMBODIMENTS

The present invention will be described in detail with reference to the following examples; however, the invention is not limited to these examples. In the following examples, schizophyllan, and schizophyllan to which a functional molecule is linked may also be referred to as "SPG" and "modified SPG", respectively. Polydeoxyadenine may also be referred to as "poly(dA)". Polyethylene glycol may also be referred to as "PEG".

Example 1

1. Synthesis of a Modified SPG

SPG having a triple helical structure was produced according to a standard method described in A.C.S. 38 (1), 253 (1997); *Carbohydrate Research,* 89, 121-135 (1981). Specifically, *Schizophyllum commune* Fries (ATCC 44200)

obtained from ATCC (American Type Culture Collection) was cultured under static conditions for 7 days using a minimum medium. Subsequently, supernatant obtained by centrifugation of cellular components and insoluble residue was sonicated, thereby producing SPG having a triple helical structure and a molecular weight of 450,000. The thus-obtained SPG may also be referred to as "SPG1" below.

Next, 100 mg of the obtained SPG1 having a molecular weight of 450,000 was dissolved in 80 ml of distilled water. 26.4 mg of sodium periodate (0.8 equivalents relative to the side-chain glucose units) was dissolved in a small amount of distilled water, and slowly added to the SPG1 solution while stirring and cooling to 4° C. The resulting reaction mixture was dialyzed with a dialysis membrane (exclusion limit: 14,000) and freeze-dried, thereby producing a white solid (SPG in which aldehyde groups were incorporated). Each of peptides, spermine, and PEG was linked to the thus-obtained compound.

Peptide Linking

The white solid obtained above was dissolved in 35 ml of dimethyl sulfoxide; 2-aminoethanol (a large excess) was added, and the mixture was stirred for 2 days at room temperature; subsequently, 300 mg of sodium borohydride (a large excess) was added to the stirred mixture. The resulting reaction mixture was dialyzed with a dialysis membrane (exclusion limit: 14,000) and freeze-dried, thereby producing a white solid. Peptides were linked to the thus-obtained SPG in which amino groups were incorporated, according to the following method.

The peptides used were as follows: R8 (amino acid sequence: CRRRRRRRR (SEQ ID NO. 1)) ("R8" disclosed as SEQ ID NO: 20); tat (amino acid sequence: CGGSGRK-KRRQRRRPPQ (SEQ ID NO. 2)); and RGD (amino acid sequence: CRGD (SEQ ID NO. 19)). These peptides were linked to the SPG in which amino groups were incorporated. Specifically, the thiol moiety of each of the peptides and the amino moiety incorporated into the SPG were linked via N-succinimidyl 3-maleimidopropionate (SMP) used as a linker (see Takahisa Anada et al., *Journal of Controlled Release*, Volume 108, Issues 2-3, 28 Nov. 2005, Pages 529-539; and Matsumoto Takahiro, et al., *Biochim Biophys Acta*, 1670 (2), (2004), 91-104).

The thus-obtained peptide R8-modified SPG ("R8" disclosed as SEQ ID NO: 20), peptide tat-modified SPG, and peptide RGD-modified SPG are hereinafter referred to as "SPG2", "SPG3", and "SPG4", respectively.

Spermine Linking

Reductive amination of the white solid obtained above and spermine (Sigma Co.; formula: $NH_2(CH_2)_3NH(CH_2)_4NH(CH_2)_3NH_2$) was performed, thereby linking the aldehyde moiety incorporated into the SPG to the amino moiety of spermine. The amino moiety of spermine and the aldehyde moiety incorporated into the SPG were linked via the reductive amination reaction (see Matsumoto Takahiro et al., *Biochim Biophys Acta*, 1670(2), (2004), 91-104; and Nagasaki Takeshi et al., *Bioconjugate Chemistry* 2004, vol. 15, pp. 249-259).

The thus-obtained spermine-modified SPG is hereinafter referred to as "SPG5".

PEG Linking

Reductive amination of the white solid obtained above and PEG in which amino groups were incorporated (methoxypolyethlene glycol amine, average molecular weight: 5,000; Sigma Co., formula: $H_2NCH_2CH_2(OCH_2CH_2)_nOCH_3$) was performed, thereby linking the aldehyde moiety incorporated into the SPG to the amino moiety of the PEG (see Ryouji Karinaga, *Biomaterials*, 2005 August; 26 (23): 4866-73).

The thus-obtained PEG-modified SPG is hereinafter referred to as "SPG6".

2. Synthesis of Double-Stranded RNA Having PolydA at the 5' End of the Sense Strand A 67-base-long DNA-RNA chimera polynucleotide having a 40-base-long DNA strand (polyadenine; polyA40) (SEQ ID NO: 15) at the 5' end of a 27-base-long RNA strand was synthesized as a sense strand. A 27-base-long antisense RNA having a sequence completely complementary to the RNA region in the 67-base-long DNA-RNA chimera polynucleotide was synthesized. By annealing these two strands, a double-stranded oligonucleotide (a DNA-bound double-stranded RNA) having the region of a 40-base-long single-stranded polydeoxyadenine (SEQ ID NO: 15) was formed.

Additionally, a DNA-RNA chimera polynucleotide (having a linker) was synthesized by inserting the linker X, represented by the formula shown below, between the DNA region and RNA region in the same DNA-RNA chimera polynucleotide as above.

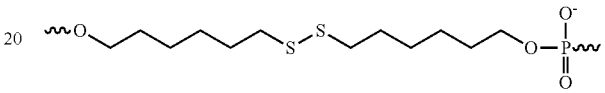

The resulting DNA-RNA chimera polynucleotide (having a linker) was annealed with a 27-base-long antisense RNA having a sequence completely complementary to the RNA region in the chimera polynucleotide, thereby synthesizing a DNA-RNA chimera double-stranded oligonucleotide having the region of a 40-base-long single-stranded polydeoxyadenine (SEQ ID NO: 15), and wherein the DNA and double-stranded RNA were linked via a linker.

A 27-base-long double-stranded RNA with no DNA region was also synthesized as a control. A commonly used 21-base-long siRNA was also used as a control. The polynucleotide used herein was a double-stranded polynucleotide including an antisense RNA having a sequence homologous to the *Renilla luciferase* gene, and designed to induce RNA interference in cells.

In the synthesis described above, the concentration of the single-stranded RNA was determined by measuring the absorbance at 260 nm using a UV spectrum detector. The annealing of double-stranded RNAs was performed by mixing equimolar amounts of a sense oligonucleotide and an antisense oligonucleotide in a universal buffer (Hayashi-Kasei Co., Ltd.), heating the mixture for 2 minutes at 92° C., and then slowly lowering the temperature to 4° C.

The sequences of the RNAs and DNA-RNA chimera oligonucleotides used are as follows:

Sense strands:

```
                                          (SEQ ID NO. 3)
  21s:
  5'-GGCCUUUCACUACUCCUACGA-3'

(SEQ ID NO. 4)
  27s:
  5'-CUGGCCUUUCACUACUCCUACGAGCAC-3'

(SEQ ID NO. 5)
  pA40-27R1:
  5'-(a)40-CUGGCCUUUCACUACUCCUACGAGCAC-3'
  ("pA40" is disclosed as SEQ ID NO: 15)

(SEQ ID NO. 6)
  pA40-27R2:
  5'-(a)40-X-CUGGCCUUUCACUACUCCUACGAGCAC-3'
  ("pA40" and "(a)40" are disclosed as
  SEQ ID NO: 15)
```

Antisense strands:

```
                                              (SEQ ID NO. 7)
    21as:    3'-GACCGGAAAGUGAUGAGGAUG-5'

(SEQ ID NO. 8)
    27as:    3'-GACCGGAAAGUGAUGAGGAUGCUCGUG-5'
```

In the sequences of the sense strands, "(a)40" means a 40-base-long polyadenine (SEQ ID NO: 15). In the sense strand pA40-27R2, ("pA40" is disclosed as SEQ ID NO: 15), "X" denotes the linker X shown above.

3. Formation of Various SPG/Double-Stranded RNA Complexes

In order to form complexes of unmodified or modified SPGs with a double-stranded RNA having polydA, various SPGs were mixed with a solution of a double-stranded RNA having polydA (the concentration of the double-stranded RNA: 10 µM; buffer: universal buffer (Hayashi-Kasei Co., Ltd.) containing 1% DMSO), and the mixtures were incubated for 3 days at 4° C. The various SPGs dissolved in DMSO (dimethyl sulfoxide) were used, and each SPG was mixed in an amount of 2 mol per mol of the double-stranded RNA having polydA. The final concentration of the DMSO in the double-stranded RNA solution was adjusted to 1 vol %. Preliminary experiments had demonstrated that the 1 vol % DMSO solution affects neither the cells nor the RNA interference effects.

FIG. 1 shows the structures of the thus-prepared various SPG/double-stranded RNA complexes. The formation of these SPG/double-stranded RNA complexes was validated using a 20% polyacrylamide gel. Specifically, 10 µl (2 µM) of each hybrid solution was applied to the 20% polyacrylamide gel, and the sample was electrophoresed for 70 minutes at 250 V. The product was subsequently stained using a silver staining kit (GE Health Care Bioscience) (see the product manual for staining conditions), and subjected to gel analysis using a Chemilmager 4000 (Alpha Innotech Corporation). The results are shown in FIG. 2. The results show that in the case of each double-stranded RNA having polydA, a band was observed at a position whose migration distance was shorter than that of the 27-base-long double-stranded RNA, demonstrating the formation of the target double-stranded RNA having polydA. Further, the various SPG/double-stranded RNA complexes remained in the wells of the polyacrylamide, demonstrating the formation of complexes between the SPG and the double-stranded RNAs having polydA.

FIG. 3 shows the results of CD spectral analysis conducted on a SPG/double-stranded RNA complex. The left graph of FIG. 3 shows the CD spectra of DNA-RNA chimera double-stranded oligonucleotides. In the SPG/double-stranded RNA complex obtained by adding SPG to the double strand, a significant change is observed in the spectrum of the double strand. This indicates that the double strand formed a complex with the SPG (the analysis was conducted at 5° C.). The right graph of FIG. 3 shows the results of examining the dissociation temperature of the formed complex using the CD spectrum. The thermodynamic behavior of the double strand can be observed from an examination of changes in the CD value at 281.6 nm due to variations in temperature. The double strand shows a decrease in the CD intensity at around 70° C., indicating the dissociation of the double strand at about 70° C. On the other hand, the SPG/double-stranded RNA complex shows an abrupt decrease in the CD intensity at around 47° C., in addition to the decrease attributed to the dissociation of the double strand. This abrupt decrease is due to the dissociation of the double strand from the complex; thus, the results suggest that the dissociation temperature of the complex is about 47° C.

4. Dicer Processing of Various SPG/Double-Stranded RNA Complexes

Dicer processing of a 27-base-long double-stranded RNA, a double-stranded RNA having polydA, and various SPG/double-stranded RNA complexes was evaluated. The Dicer cleavage experiments were performed as follows: 0.5 U recombinant Dicer (Gene Therapy Systems) and 10 µl each of the 27-base-long double-stranded RNA, double-stranded RNA having polydA, and various SPG/double-stranded RNA complexes adjusted to a final concentration of 2 µM in solutions of 20 mM Tris-HCl (pH 8.0), 15 mM NaCl, and 2.5 mM $Mg_2Cl$ were prepared in sample tubes. The samples were incubated in an incubator for 12 hours at 37° C. In order to subsequently stop the cleavage reactions by Dicer, 2 µl of Dicer Stop Solution (Gene Therapy Systems) was added into the reaction solutions, followed by the addition of 2 µl of a loading die. The resulting sample products were electrophoresed on a 20% polyacrylamide gel at 250 V for 70 minutes. The products were then stained with a silver staining kit (GE Health Care Bioscience) (see the product manual for staining conditions), and subjected to gel analysis using a Chemilmager 4000 (Alpha Innotech corporation). As a control, a siRNA (21 siRNA) consisting of a 21-base-long double-stranded RNA not processed by Dicer was used.

The results are shown in FIG. 4. The results show that in the case of 27s/27as, which is the 27-base-long double-stranded RNA, and in the case of pA40-27R1/27as ("pA40" is disclosed as SEQ ID NO: 15), which has the region of a 40-base-long single-stranded polydeoxyadenine (SEQ ID NO: 15) at the 5' end of the sense strand, bands were observed at positions similar to those of the 21-base-long siRNA in the presence of recombinant Dicer. This strongly indicates that 21-base-long siRNAs containing a dangling end of two bases were formed by Dicer cleavage. In the case of the complexes formed between SPGs (1 to 6) and pA40-27R1/27as ("pA40" is disclosed as SEQ ID NO: 15), it is also strongly indicating that the complexes have been processed by recombinant Dicer and consequently 21-base-long siRNAs containing a dangling end of two bases were formed.

It was found from these results that 27-base-long double-stranded RNAs, even when they contained a long single-stranded polydeoxyadenine or SPGs (SPG/double-stranded RNA complexes), were processed into 21-base-long siRNAs by recombinant Dicer.

5. Resistance to Enzymatic Degradation of Various SPG/Double-Stranded RNA Complexes (5-1) Resistance to Enzymatic Degradation of SPG/Double-Stranded RNA (27-Base-Long) Complexes The nuclease resistance of a 27-base-long double-stranded RNA, a double-stranded RNA having polydA, and various SPG/double-stranded RNA complexes (hereinafter also referred to as the "test samples") was evaluated. The experiments were performed as follows: Each of the test samples adjusted to a final concentration of 2 µM was incubated at 37° C. in an RPMI-1640 medium (Invitrogen) containing 10% FBS (Sanko Junyaku, Co., Ltd.) (final volume: 110 µl). After 0 h, 0.5 h, 1 h, 2 h, 4 h, 6 h, 8 h, 12 h, 24 h, and 48 h, each 10 µl aliquot was sampled and inserted into a sample tube containing 2 µl of a loading die. In order to subsequently stop the degradation reaction, the sample taken was immediately frozen in liquid nitrogen and preserved at −20° C. The resulting sample product was electrophoresed on a 20% polyacrylamide gel at 250 V for 70 minutes. The product was then stained with a silver staining kit (GE Health Care Bioscience) (see the product manual for staining conditions), and subjected to gel analysis using a Chemilmager 4000 (Alpha Innotech Corporation). For comparison, the resistance to enzymatic degradation of a 21-base-long siRNA having a dangling end of two bases at the 3' end, which is commonly used in siRNA methods, was also evaluated in the same manner as described above. The results are shown in FIG. 5.

As a result, the 21-base-long double-stranded RNA (21 siRNA) having a dangling end of two bases was rapidly digested in the medium containing 10% FBS; whereas the 27-base-long double-stranded RNA, double-stranded RNA having polydA, and various SPG/double-stranded RNA complexes were found to have very high resistance to enzymatic degradation. The results also indicated that the double-stranded RNA having polydA exhibited resistance to enzymatic degradation higher than that of the 27-base-long double-stranded RNA, and that the various SPG/double-stranded RNA complexes exhibited resistance to enzymatic degradation even higher than that of the double-stranded RNA having polydA. In particular, it became evident that the SPG/double-stranded RNA complex was hardly digested by nuclease even after 48 hours. These results demonstrated that the double-stranded RNA having polydA and various SPG/double-stranded RNA complexes had very high stability in a serum-containing medium.

(5-2) Resistance to Enzymatic Degradation of SPG/Double-Stranded RNA (21-Base-Long) Complexes The nuclease resistance of a 21-base-long double-stranded RNA, a double-stranded RNA having polydA, a double-stranded RNA having polydT, and various SPG/double-stranded RNA complexes (dA, dT; hereinafter also referred to as the "test samples") was evaluated.

The sequences of the RNAs and DNA-RNA chimera oligonucleotides used are as follows:
Sense Strands:

```
                                          (SEQ ID NO. 9)
    21s:      5'-GGUGGUGACGAUCUGGGCUUU-3'

(SEQ ID NO. 10)
    pA40-21:  5'-(a)40-GGUGGUGACGAUCUGGGCUUU-3'
              ("pA40" is disclosed as SEQ
              ID NO: 15)

(SEQ ID NO. 11)
    pT40-21:  5'-(t)40-GGUGGUGACGAUCUGGGCUUU-3'
              ("pT40" is disclosed as SEQ
              ID NO: 16)
```

Antisense Strand:

```
                                          (SEQ ID NO. 12)
    21as:     3'-UUUCGGGUCUAGCAGUGGUGG-5'
```

In the sequences of the sense strands, "(a)40" means a 40-base-long polydA (SEQ ID NO: 15), and "(t)40" means a 40-base-long dT (SEQ ID NO: 16).

The experiments were performed as follows: Each of the test samples adjusted to a final concentration of 40 nM was incubated at 37° C. in an RPMI-1640 medium (Sigma) containing 10% FBS (MP Biomedicals, Inc.) (final volume: 100 μl). After 0 h, 0.25 h, 3 h, 6 h, 12 h, 24 h, and 48 h, the sample was collected, and frozen at −80° C. in order to stop the degradation reaction. The resulting test sample was extracted with phenol, treated with chloroform, and purified by ethanol precipitation. The test sample was then electrophoresed on a 20% polyacrylamide gel at 250 V for 60 minutes. Subsequently, the sample was stained with SYBER Gold (Invitrogen), and subjected to gel analysis using a luminescent image analyzer LAS-3000 (Fujifilm). The results are shown in FIG. 6.

The 21-base-long double-stranded RNA containing a dangling end of a single base (naked siLamin 21 bp), the double-stranded RNA not forming a complex (naked siLamin dA40) ("dA40" is disclosed as SEQ ID NO: 15), and the SPG/double-stranded RNA complex having polydT (SPG complex siLamin dT40) ("dT40" is disclosed as SEQ ID NO: 16) were rapidly digested in the 10% FBS-containing medium; whereas the SPG/double-stranded RNA complex having polydA (SPG complex siLamin dA40) ("dA40" is disclosed as SEQ ID NO: 15) was found to have high resistance to enzymatic degradation.

6. Cytotoxicity of PolydA-Double-Stranded RNA/SPG Complexes (6-1) Cytotoxicity of PolydA-Double-Stranded RNA (27-Base-Long)/SPG Complexes on HeLa Cells Cytotoxicity on HeLa cells of a 27-base-long double-stranded RNA, a double-stranded RNA having polydA, and various SPG/double-stranded RNA complexes (hereinafter also referred to as the "test samples") was evaluated. HeLa cells (human cervical cancer cells; Institute of Development, Aging and Cancer, Tohoku University) adjusted to $1 \times 10^5$ cells/ml prior to the experiments were seeded on a 96-well plate at 100 μl per well, and incubated at 37° C. overnight. On the next day, the old medium in the wells was removed, and a fresh, antibiotic-free medium was added at 90 μl per well. In order to evaluate the intracellular toxicity, the cytotoxicity of each test sample was evaluated by actively introducing test samples into cells using Lipofectamine™2000 (Invitrogen). Each test sample was mixed and complexed with Lipofectamine™2000 (Invitrogen) such that the final concentrations of the test sample were 0 nM, 0.2 nM, 0.5 nM, 1 nM, 2 nM, 5 nM, 10 nM, 20 nM, and 50 nM. Ten microliters of the complex was added to the HeLa cells in 90 μl medium above, such that the final volume per well was 100 μl. The test sample was complexed with Lipofectamine™2000 by mixing 5 μl of an aqueous solution of the test sample with 5 μl of an OptiMem solution of Lipofectamine™2000 (0.2 μl) per well, and incubating the mixture for 30 minutes at room temperature. The HeLa cells to which the test sample was introduced were incubated for 48 hours at 37° C. in the presence of 5% $CO_2$. Fifty microliters of the CellTiter-Glo Reagent in the CellTiter-Glo Luminescent Cell Viability Assay (Promega) was subsequently added to each well and agitated for about 60 minutes. The level of luminescence in each well was then measured using a luminometer (MicroLumat LB96p; Berthold). Since the level of luminescence measured is dependent upon the ATP present in viable cells, the cell viability per well was determined by calculating the level of luminescence of the cell to which each test sample was introduced relative to the level of luminescence of control cells (at an RNA concentration of 0 nM and Lipofectamine™2000 concentration of 0 μl; the viability of the control cells is taken as 100%) (see the manual of Promega CellTiter-Glo Luminescent Cell Viability Assay).

FIG. 7 shows the cell viabilities measured at a maximum concentration of 10 nM of the test samples used in this experiment. As a result, all of the SPG/double-stranded RNA complexes exhibited cytotoxicity within a sufficiently acceptable range.

(6-2) RNA Interference effect of poly(dA)-Double-Stranded RNA (21-Base-Long)/SPG Complex A 21-base-long double-stranded RNA and a complex of a double-stranded RNA having poly(dA) (hereinafter also referred to as the "test sample") was evaluated for its RNA interference effects using Lamin A/C, which is a component of the nuclear membrane, as a target gene. The sequences of the RNAs and DNA-RNA chimera oligonucleotides used are as given in Section (5-2) above.

RAW 264.7 cells (macrophage-like cells derived from mice) adjusted to $5 \times 10^4$ cells/ml prior to the experiments were seeded on a 96-well plate at 100 µl per well, and incubated at 37° C. overnight. On the next day, the old medium in the wells was removed, and 90 µl of a fresh medium was added; 10 µl of a solution of the complex between SPG and the double-stranded RNA having poly (dA) adjusted to a predetermined concentration was added to each well containing RAW 264.7 cells. The final concentration of the complex between SPG and the double-stranded RNA having poly(dA) was adjusted to 600 nM (in terms of the siRNA concentration). After introduction of the test sample, the cells were incubated for 24 hours at 37° C. and frozen at –80° C. The total RNA was then extracted using an RNeasy mini kit (QIAGEN), and cDNA was prepared using a PrimeScript RT reagent Kit (Takara Bio, Inc.). The Real Time PCR reaction was performed using a SYBR Premix Ex Taq (Takara Bio, Inc.), and the mRNA level of Lamin A/C was measured using a Smart Cycler II (Cepheid; sold by Takara Bio, Inc.). The level of mRNA expression of Lamin A/C was corrected with GAPDH, which is a general housekeeping gene, thereby determining the level of mRNA expression of Lamin A/C. The results are shown in FIG. 8.

As controls, naked siRNA dA40 (Lamin A/C) ("dA40" is disclosed as SEQ ID NO: 15), SPG only, and a mixture of SPG and naked siRNA dA40 (Lamin A/C) ("dA40" is disclosed as SEQ ID NO: 15) prepared immediately before the addition into the cells were evaluated for their RNA interference effects. The results are shown in FIG. 8. No RNA interference effects were observed for the naked siRNA dA40 (Lamin A/C) ("dA40" is disclosed as SEQ ID NO: 15), SPG only, and the mixture of SPG and naked siRNA dA40 (Lamin A/C) ("dA40" is disclosed as SEQ ID NO: 15) prepared immediately before the addition into the cells; however, only the complex between SPG and the double-stranded RNA having polydA was found to have RNA interference effects. Consequently, the SPG used alone did not have inhibitory effects on the mRNA expression of Lamin A/C in RAW 264.7 cells, nor did the naked siRNA have such inhibitory effects.

7. RNA Interference Effects of PolydA-Double-Stranded RNA/SPG Complexes

A 27-base-long double-stranded RNA, a double-stranded RNA having polydA, and various SPG/double-stranded RNA complexes (hereinafter also referred to as the "test samples") were evaluated for their RNA interference effects using *Renilla luciferase* as a target gene. HeLa cells (human cervical cancer cells; Institute of Development, Aging and Cancer, Tohoku University) adjusted to $1 \times 10^5$ cells/ml prior to the experiments were seeded on a 96-well plate at 100 µl per well, and incubated at 37° C. overnight. On the next day, the old medium in the wells was removed, and a fresh, antibiotic-free medium was added at 80 µl per well. A complex solution of a vector expressing the firefly and *Renilla luciferase* (psiCHECK™-2 Vector; Promega) and Lipofectamine™2000 (trade name; Invitrogen) was added at 10 µl per well containing the HeLa cells. The amount of the expression vector was adjusted to 0.02 µg per well, and the amount of Lipofectamine™2000 was adjusted to 0.2 µl per well; OptiMem (Invitrogen) was used to adjust the amount to a necessary level. To form a complex, the expression vector and Lipofectamine™2000 were mixed using OptiMem, and then the mixture was incubated for 30 minutes at room temperature. After the addition of the complex solution, the cells were incubated for 4 hours at 37° C. in the presence of 5% $CO_2$. After incubation, each test sample was complexed with Lipofectamine™2000 (Invitrogen) to prepare complex solutions such that the final concentrations of the test sample were 0.2 nM and 0.5 nM. Ten microliters of each complex solution was added to the HeLa cells transfected with the expression vector. The final volume per well was 100 µl. The complex solutions of the test sample and Lipofectamine™2000 were prepared by mixing 5 µl of an aqueous solution of the test sample with 5 µl of an OptiMem solution of Lipofectamine™2000 (0.2 µl) per well, and incubating the mixture for 30 minutes at room temperature. After the introduction of the test sample, the cells were incubated for 48 hours. Using the Dual-Glo™ Luciferase Assay System (Promega), the levels of expression of firefly and *Renilla luciferase* were measured with a luminometer (MicroLumat LB96p; Berthold), and the level of expression (%) of *Renilla luciferase* was determined based on the level of expression of firefly luciferase as a control.

The measured RNA interference effects are given in FIG. 9. FIG. 9 shows the RNA interference effects of the various SPG/double-stranded RNA complex samples when added in a concentration of 0.5 nM. For comparison, FIG. 9 also shows the RNA interference effects measured for a 21-base-long siRNA having a dangling end of two bases at the 3' end, which is used in siRNA methods, a 27-base-long double-stranded RNA, and a double-stranded RNA having polydA. The results show that the SPG/double-stranded RNA complex exhibited reduced RNA interference effects as compared to the 27-base-long double-stranded RNA. The reason for this is believed to be that the addition of SPG1 weakened the interaction between the oligonucleotide and Lipofectamine, thus making the cellular uptake lower than that of the 27nt dsRNA, resulting in a lowered ability to inhibit gene expression as compared to that of the 27nt dsRNA. On the other hand, the various SPG/double-stranded RNA complexes prepared using modified SPGs (SPG2 to SPG6) obtained by modifying SPG with a functional molecule exhibited RNA interference effects substantially equivalent to the ability of the 27-base-long double-stranded RNA to inhibit gene expression. This revealed that these SPG/double-stranded RNA complexes possessed an enhanced ability to inhibit gene expression as compared to that of the SPG/double-stranded RNA complex prepared using SPG1. It is believed that these results are attributed to the fact that the functional molecule introduced to the SPG enhanced the cellular uptake.

A summary of the above results revealed that the various SPG/double-stranded RNA complexes exhibit excellent resistance to enzymatic degradation and little toxicity, and therefore, possess enhanced durability and safety as compared to general siRNAs. The above results also demonstrated that, by modifying SPG with various functional groups, it is possible to construct SPG/double-stranded RNA complexes that can reach into cells by themselves, without using a gene transfection reagent having high cytotoxicity.

Reference Test Example 1

The following test was conducted to demonstrate that the technique disclosed in Non-Patent Document 4 (Kazuo Sakurai, *Polym. Preprints*, Jpn., volume 49, page 4054, 2000) cannot yield high transfection efficiency when applied to double-stranded RNAs having RNA interference effects.

EGFP (Enhanced Green Fluorescent Protein) is a fluorescent protein consisting of 238 amino acids. When the genetically engineered EGFP gene is transfected into living cells using the pEGFP vector, it is evenly distributed throughout the cells. The EGFP gene forms a chromophore by exposure to excitation light to produce fluorescence (FIG. 11).

The pEGFP vector was fragmented using the restriction enzyme Sph I, and an adapter ODN (deoxynucleotide), to which the 3' end of the vector could be hybridized, was linked to polydA80mer ("dA80" is disclosed as SEQ ID NO: 17). The resulting product was complexed with SPG (FIG. 10).

To RAW cells forced to express Dectin-1 were added DNAs of various lengths (for example, 800 to 2,500 bp) having complexed ends, and DNA side chains were chemically modified with a fluorescent substance, Alexa (FIG. 12). The relationship between the rate of cell transfection and the length of the DNA was examined by counting the number of cells where Alexa was detected. The results are shown in FIG. 13. In FIG. 13, the rate of cell transfection of the CMV-EGFP prepared according to the method of FIG. 10 is shown as 1.

FIG. 13 shows that the transfection efficiency decreases as the length of the double-stranded DNA becomes greater. That is, the test method was indicated to be of little practical use as a delivering technique for transfecting long pDNAs into cells.

BRIEF DESCRIPTION OF THE DRAWINGS

FIG. 1 discloses "SPG2" as SEQ ID NO: 1, "SPG3" as SEQ ID NO: 2, "SPG4" as SEQ ID NO: 19 and "dA(40)" as SEQ ID NO: 15.

FIG. 2 discloses "pA40" as SEQ ID NO: 15.

FIG. 4 discloses "pA40" as SEQ ID NO: 15.

FIG. 5 discloses "pA40" as SEQ ID NO: 15.

FIG. 6 discloses "dA 40" as SEQ ID NO: 15 and "dT 40" as SEQ ID NO: 16.

FIG. 7 discloses "pA40" as SEQ ID NO: 15.

FIG. 8 discloses "dA40" as SEQ ID NO: 15.

FIG. 9 discloses "pA40" as SEQ ID NO: 15.

FIG. 10 discloses "AAAAAAAAAAAAAA" as SEQ ID NO: 18 and "(dA)$_{80}$" as SEQ ID NO: 17.

SEQUENCE LISTING FREE TEXT

Figure 1:
FIG. 1 shows the structures of various SPG/RNA complexes formed.
Figure 1:
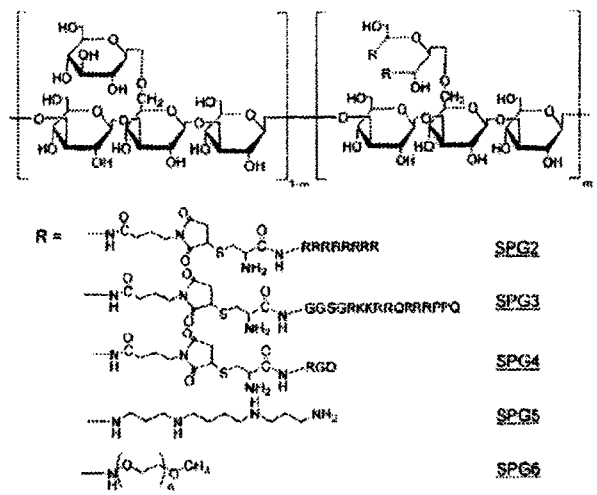
Figure 1:
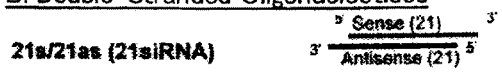
Figure 1:
Figure 1:
Figure 1:
Figure 1:
Figure 1:
Figure 2:
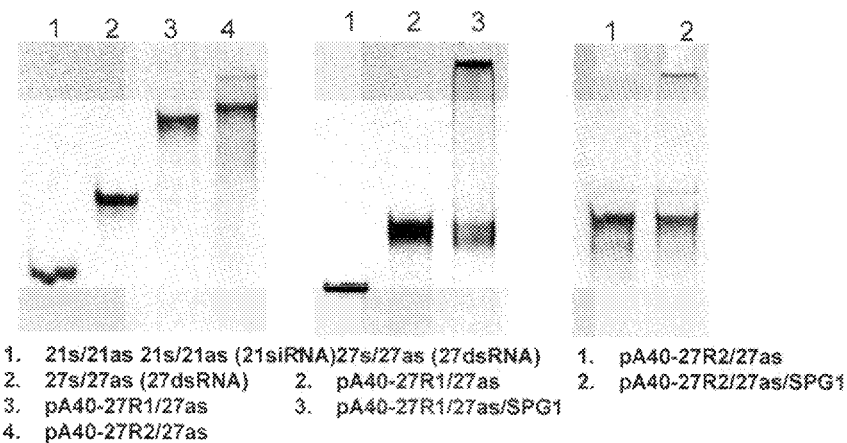
FIG. 2 shows the results validating whether the various SPG/RNA complexes were formed or not.
Figure 3:
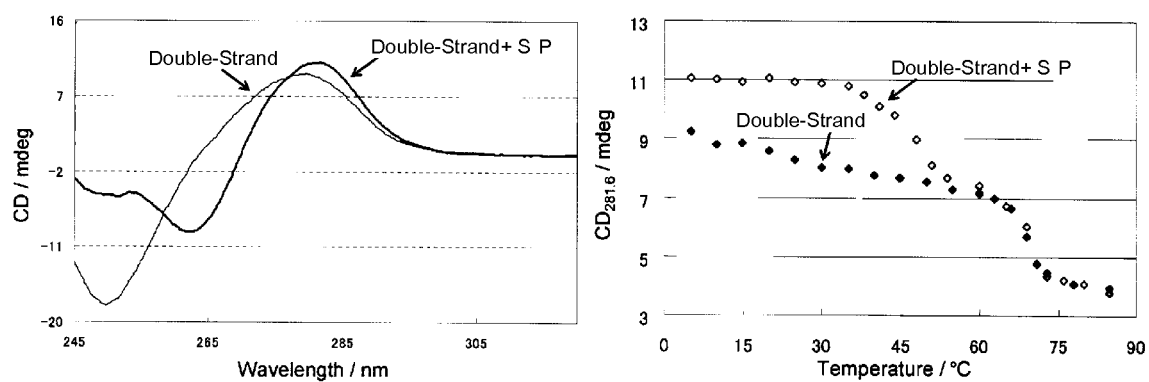
FIG. 3 shows the results validating whether a SPG/RNA complex was formed or not using CD spectral analysis (left graph); and the results validating the dissociation temperature of the SPG/RNA complex using CD spectral analysis (right graph).
Figure 4:
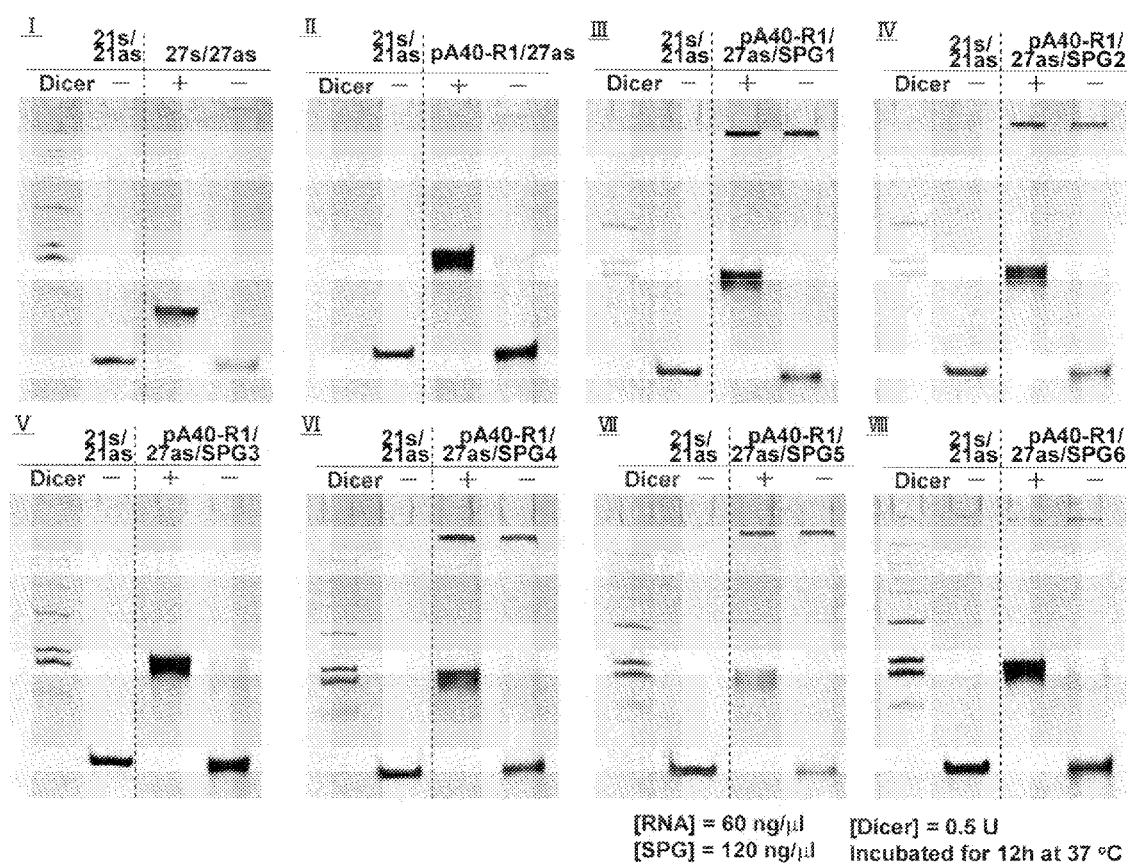
FIG. 4 shows the results of evaluating the Dicer processing of various SPG/RNA complexes.
Figure 5:
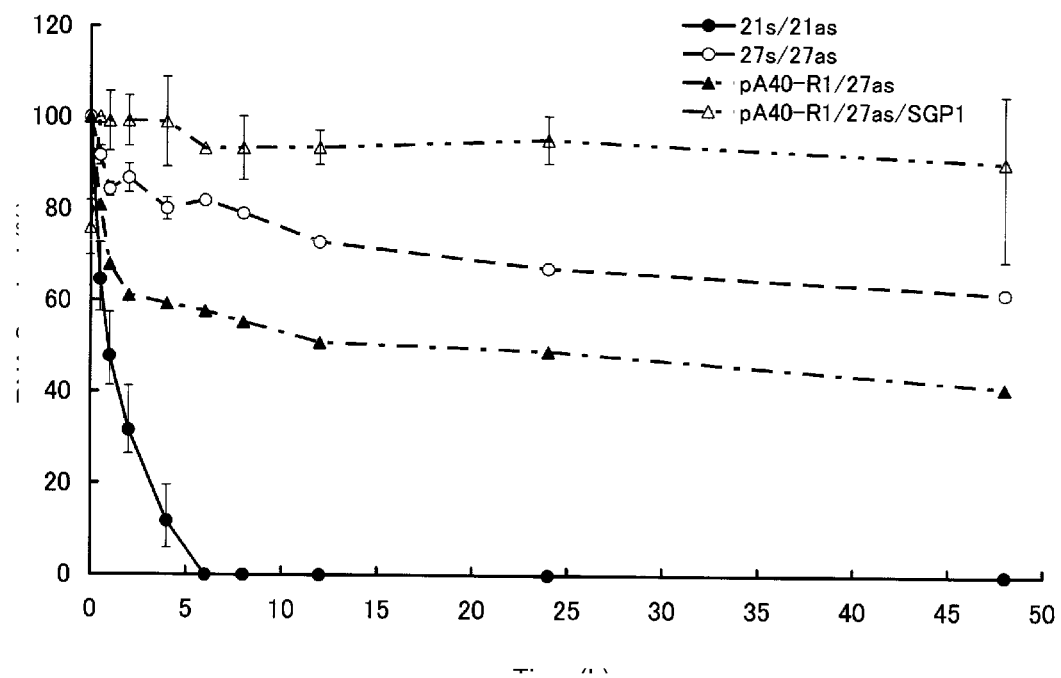
FIG. 5 shows the results of evaluating the nuclease resistance of various SPG/RNA (27-base-long) complexes.
Figure 6:
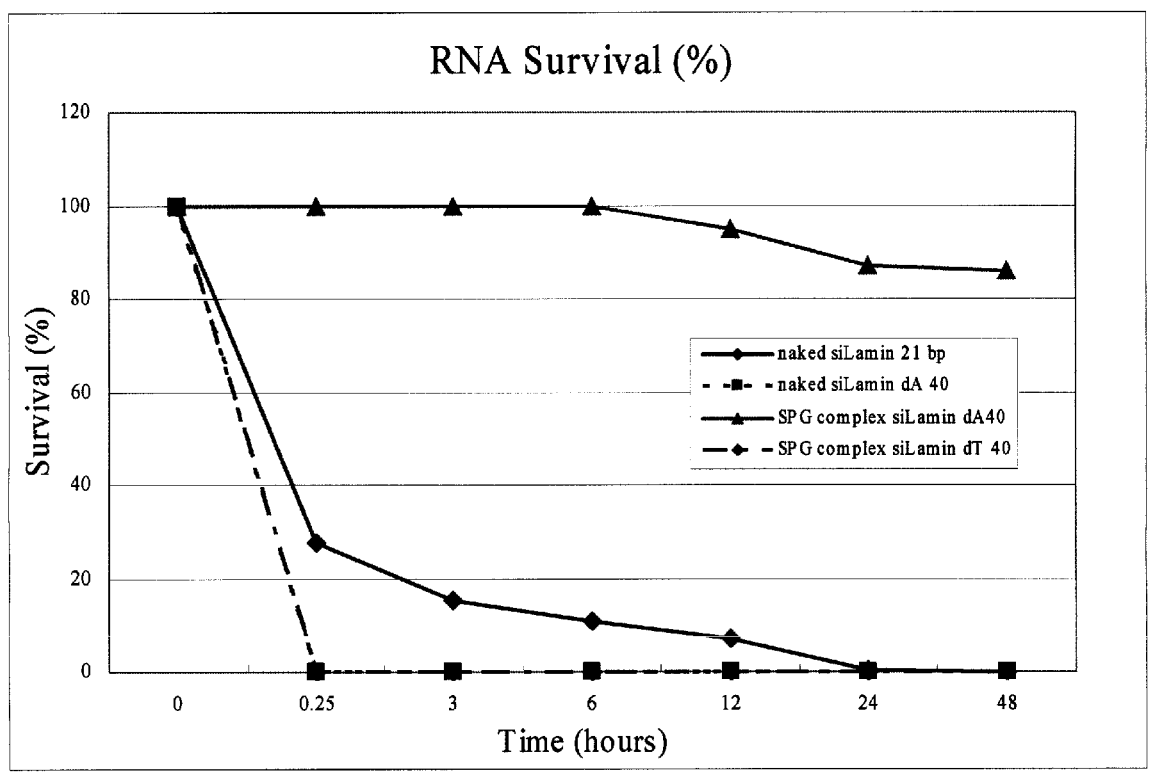
FIG. 6 shows the results of evaluating the nuclease resistance of various SPG/RNA (21-base-long) complexes.
Figure 7:
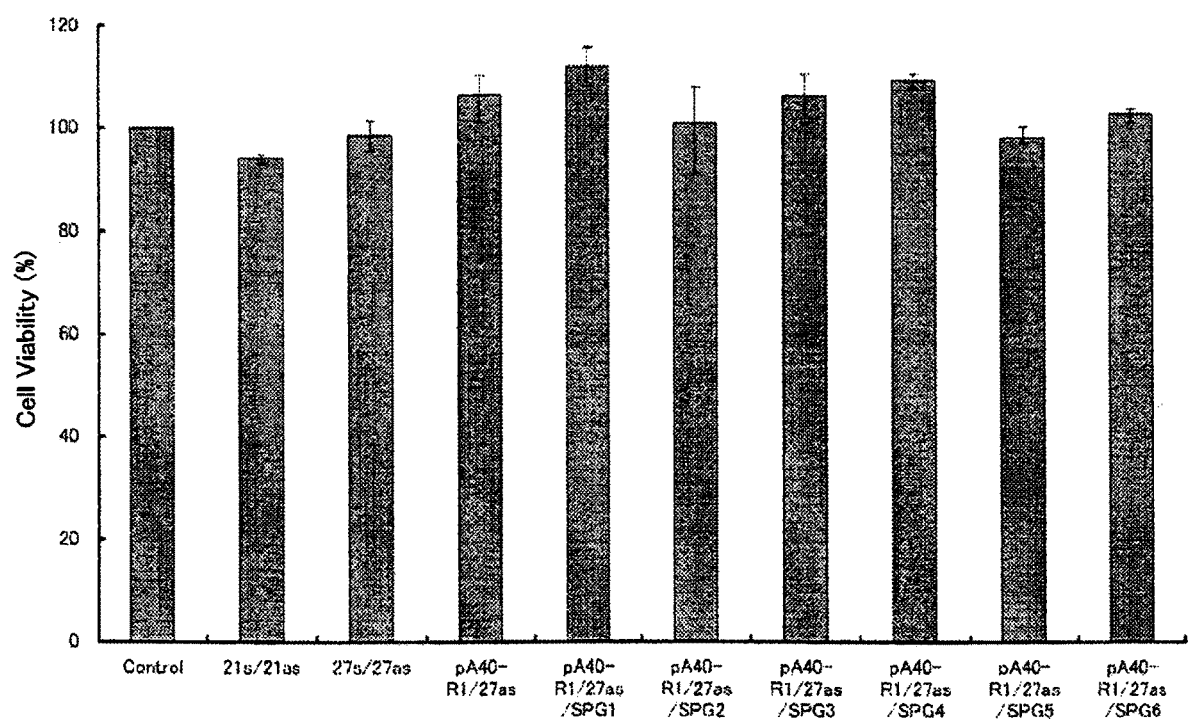
FIG. 7 shows the results of evaluating the cytotoxicity of various SPG/RNA (27- base-long) complexes.
Figure 8:
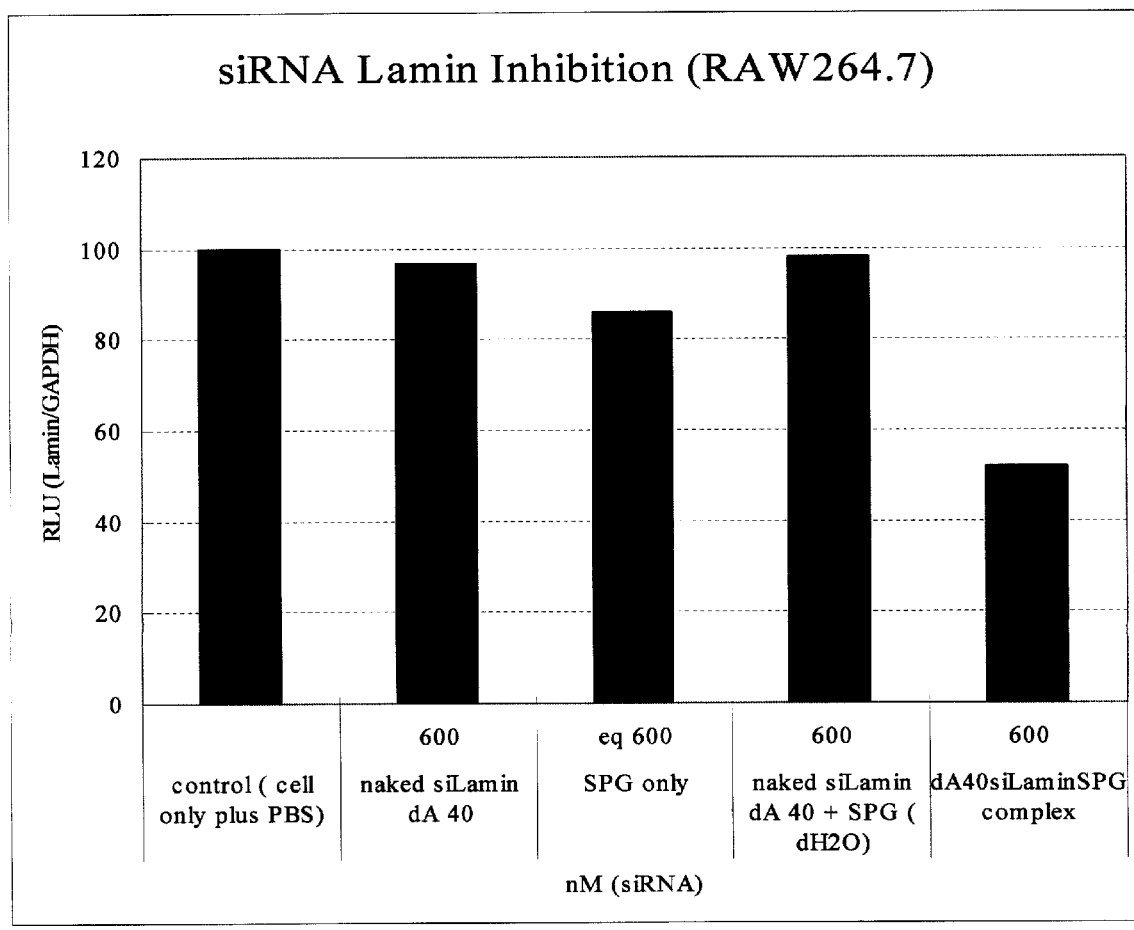
FIG. 8 shows the results of evaluating the cytotoxicity of various SPG/RNA (21- base-long) complexes.
Figure 9:
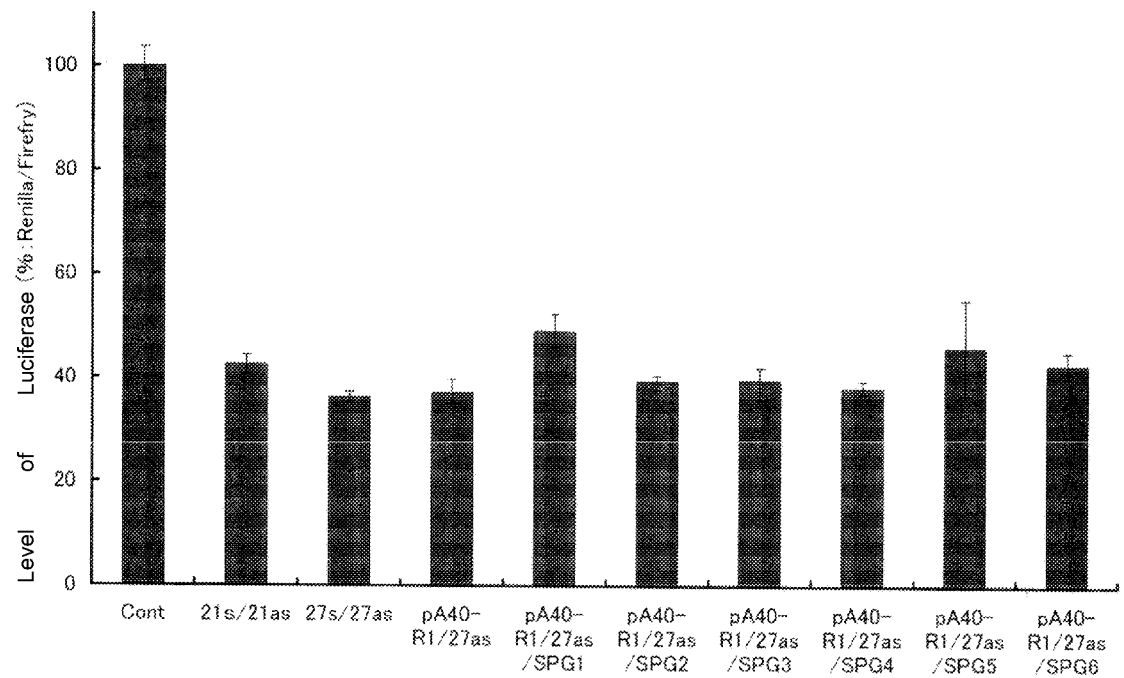
FIG. 9 shows the results of evaluating the RNA interference effects of various SPG/RNA complexes.
Figure 10:
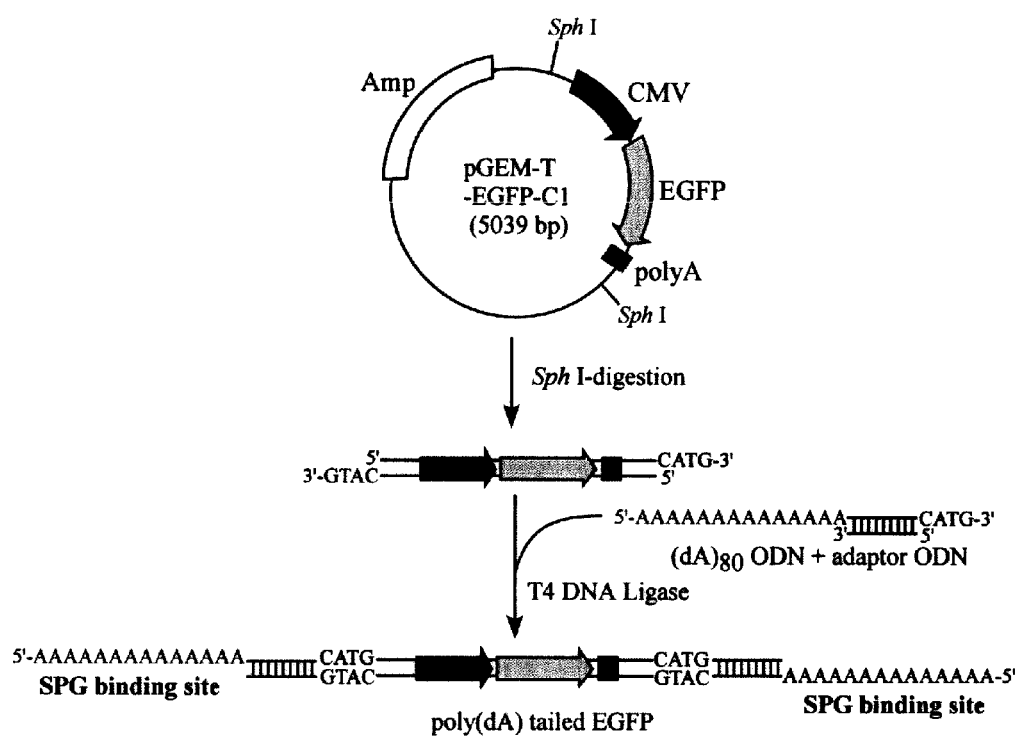
FIG. 10 is a schematic diagram showing the method for preparing CMV-EGFP.
Figure 11:
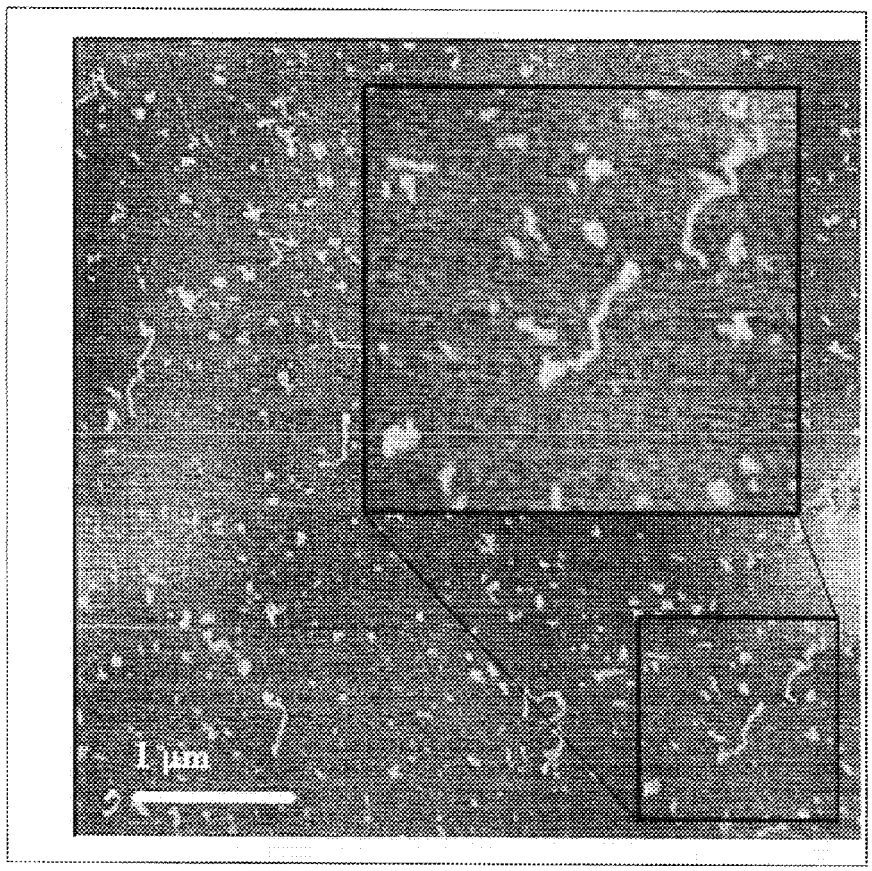
FIG. 11 shows a micrograph of cells taken when the EGFP gene was transfected into living cells using the pEGFP vector.
Figure 12:
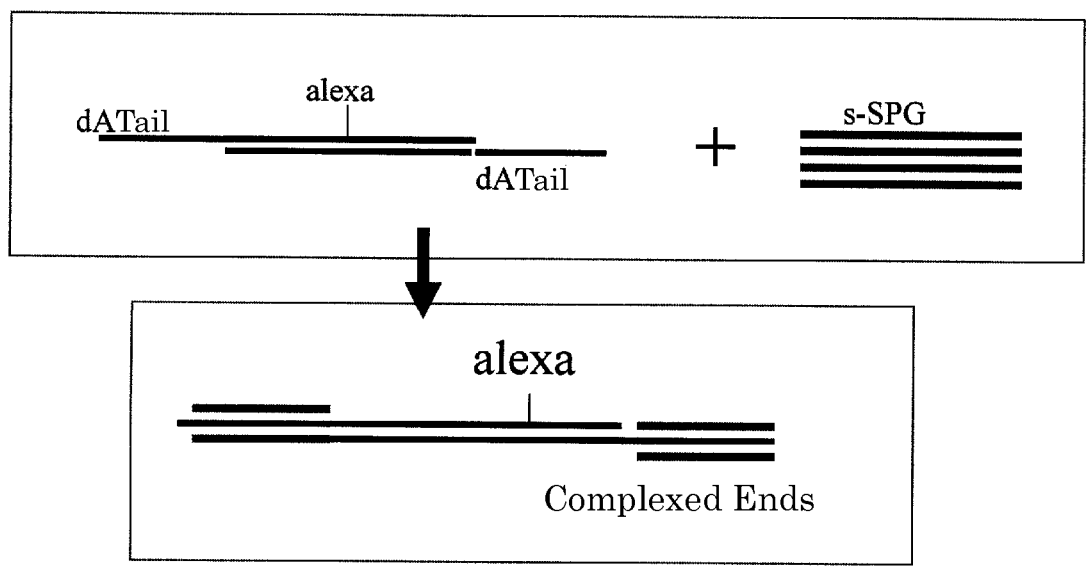
FIG. 12 is a schematic diagram showing the method for preparing the DNAs having complexed ends and chemically modified with the fluorescent substance, Alexa, which were used in Reference Test Example 1.
Figure 13:
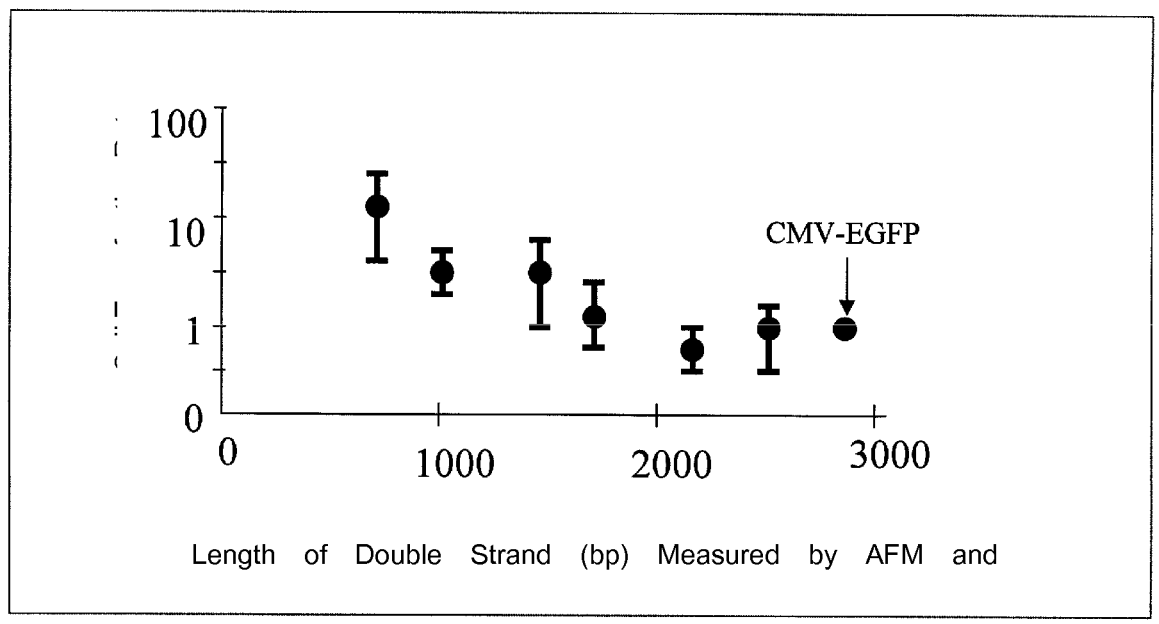
FIG. 13 shows the results obtained in Reference Test Example 1.

SEQ ID NO. 1 shows the sequence of R8 ("R8" disclosed as SEQ ID NO: 20).

SEQ ID NO. 2 shows the sequence of tat.

SEQ ID NO. 3 shows the sequence of 21S.

SEQ ID NO. 4 shows the sequence of 27s.

SEQ ID NO. 5 shows the sequence of the region of pA40-27R1 RNA ("pA40" is disclosed as SEQ ID NO: 15)

SEQ ID NO. 6 shows the sequence of the region of pA40-27R2 RNA ("pA40" is disclosed as SEQ ID NO: 15).

SEQ ID NO. 7 shows the sequence of 21as.

SEQ ID NO. 8 shows the sequence of 27as.

SEQ ID NO. 9 shows the sequence of 21s.

SEQ ID NO. 10 shows the sequence of pA40-21 ("pA40" is disclosed as SEQ ID NO: 15).

SEQ ID NO. 11 shows the sequence of pT40-21 ("pT40" is disclosed as SEQ ID NO: 16).

SEQ ID NO. 12 shows the sequence of 21as.

SEQUENCE LISTING

```
<160> NUMBER OF SEQ ID NOS: 20

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      R8 peptide

<400> SEQUENCE: 1

Cys Arg Arg Arg Arg Arg Arg Arg Arg
1               5
```

```
<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      tat peptide

<400> SEQUENCE: 2

Cys Gly Gly Ser Gly Arg Lys Lys Arg Arg Gln Arg Arg Pro Pro
1               5                   10                  15

Gln

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      21s oligonucleotide

<400> SEQUENCE: 3
ggccuuucac uacuccuacg a                                                   21

<210> SEQ ID NO 4
<211> LENGTH: 27
<212> TYPE: RNA
<213> ORGANISM: Artificial Sequence
<220> FEATURE:
<223> OTHER INFORMATION: Description of Artificial Sequence: Synthetic
      27s oligonucleotide

<400> SEQUENCE: 4
cuggccuuuc acuacuccua cgagcac                                             27

<210> SEQ ID NO 5
<211> LENGTH: 67
<212> TYPE: DNA
<213> ORGANISM: Artificial Sequence
<220> FEATURE:
<223> OTHER INFORMATION: Description of Artificial Sequence: Synthetic
      pA40-27R1 RNA region oligonucleotide
<220> FEATURE:
<223> OTHER INFORMATION: Description of Combined DNA/RNA Molecule:
      Synthetic pA40-27R1 RNA region oligonucleotide

<400> SEQUENCE: 5
aaaaaaaaaa aaaaaaaaaa aaaaaaaaaa aaaaaaaaa cuggccuuuc acuacuccua         60
cgagcac                                                                   67

<210> SEQ ID NO 6
<211> LENGTH: 27
<212> TYPE: RNA
<213> ORGANISM: Artificial Sequence
<220> FEATURE:
<223> OTHER INFORMATION: Description of Artificial Sequence: Synthetic
      pA40-27R2 RNA region oligonucleotide

<400> SEQUENCE: 6
cuggccuuuc acuacuccua cgagcac                                             27

<210> SEQ ID NO 7
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      21as oligonucleotide

<400> SEQUENCE: 7
guaggaguag ugaaaggcca g                                              21

<210> SEQ ID NO 8
<211> LENGTH: 27
<212> TYPE: RNA
<213> ORGANISM: Artificial Sequence
<220> FEATURE:
<223> OTHER INFORMATION: Description of Artificial Sequence: Synthetic
      27as oligonucleotide

<400> SEQUENCE: 8
gugcucguag gaguagugaa aggccag                                        27

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      21s oligonucleotide

<400> SEQUENCE: 9
gguggugacg aucgggcuu u                                               21

<210> SEQ ID NO 10
<211> LENGTH: 61
<212> TYPE: DNA
<213> ORGANISM: Artificial Sequence
<220> FEATURE:
<223> OTHER INFORMATION: Description of Artificial Sequence: Synthetic
      pA40-21 oligonucleotide
<220> FEATURE:
<223> OTHER INFORMATION: Description of Combined DNA/RNA Molecule:
      Synthetic pA40-21 oligonucleotide

<400> SEQUENCE: 10
aaaaaaaaaa aaaaaaaaaa aaaaaaaaaa aaaaaaaaaa gguggugacg aucgggcuu    60 u                                                                   61

<210> SEQ ID NO 11
<211> LENGTH: 61
<212> TYPE: DNA
<213> ORGANISM: Artificial Sequence
<220> FEATURE:
<223> OTHER INFORMATION: Description of Artificial Sequence: Synthetic
      pT40-21 oligonucleotide
<220> FEATURE:
<223> OTHER INFORMATION: Description of Combined DNA/RNA Molecule:
      Synthetic pT40-21 oligonucleotide

<400> SEQUENCE: 11
tttttttttt tttttttttt tttttttttt tttttttttt gguggugacg aucgggcuu    60 u                                                                   61

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      21as oligonucleotide
```

```
<400> SEQUENCE: 12
gguggugacg aucugggcuu u                                              21

<210> SEQ ID NO 13
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(100)
<223> OTHER INFORMATION: This sequence may encompass 20-100 nucleotides

<400> SEQUENCE: 13
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa                         100

<210> SEQ ID NO 14
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(100)
<223> OTHER INFORMATION: This sequence may encompass 10-100 nucleotides
<220> FEATURE:
<223> OTHER INFORMATION: See specification as filed for detailed
      description of substitutions and preferred embodiments

<400> SEQUENCE: 14
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa                         100

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aaaaaaaaaa aaaaaaaaaa aaaaaaaaaa aaaaaaaaaa                          40

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tttttttttt tttttttttt tttttttttt tttttttttt                          40

<210> SEQ ID NO 17
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 17
aaaaaaaaaa aaaaaaaaaa aaaaaaaaaa aaaaaaaaaa aaaaaaaaaa aaaaaaaaaa     60
aaaaaaaaaa aaaaaaaaaa                                                 80

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aaaaaaaaaa aaaa                                                       14

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Arg Gly Asp
1

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      R8 peptide

<400> SEQUENCE: 20

Arg Arg Arg Arg Arg Arg Arg Arg
1               5
```

The invention claime is:

1. A method of inhibiting expression of a target gene in a cell, comprising:
a step of introducing a polysaccharide having a β-1,3-glucan skeleton/double-stranded RNA complex into a cell;
wherein said polysaccharide is schizophyllan;
wherein the polysaccharide/double-stranded RNA complex contains double-stranded RNA having a sense strand RNA consisting of a base sequence complementary to a target sequence in a target gene and an antisense strand RNA containing a base sequence complementary to the sense strand RNA, and capable of inhibiting expression of the target gene, the sense strand RNA consisting of 21 ribonucleotides; the antisense strand RNA consisting of the same number of ribonucleotides as that of the sense strand RNA;
wherein the target gene is Lamin A/C,
wherein the double-stranded RNA has a single-stranded polydeoxyadenine bound directly or via a linker to at least one end of the sense strand and antisense strand; and
wherein the polysaccharide and the single-stranded polydeoxyadenine form a complex.

2. The method of inhibiting expression of a target gene in a cell as defined in claim 1, wherein the single-stranded polydeoxyadenine and two polysaccharides form a triple helical structure.

3. The method of inhibiting expression of a target gene in a cell as defined in claim 1, wherein the single-stranded polydeoxyadenine consists of 20 to 100 deoxyadenines as disclosed in SEQ ID NO: 13.

4. The method of inhibiting expression of a target gene in a cell as defined in claim 1, the single-stranded polydeoxyadenine is bound directly or via a linker to the 5' and/or 3' end of the sense strand RNA or antisense strand RNA.

5. The method of inhibiting expression of a target gene in a cell as defined in claim 1, the polysaccharide is a β-1,3-glucan to which a functional molecule is bound.

6. The method of inhibiting expression of a target gene in a cell as defined in claim 1, wherein the target gene of the double-stranded RNA is endogenous to a cell having a receptor that binds to the polysaccharide.

7. The method of inhibiting expression of a target gene in a cell as defined in claim 6, wherein the cell is a cell that expresses Dectin-1 on the membrane surface of the cell.

* * * * *